US012377064B2

(12) United States Patent
Carlson et al.

(10) Patent No.: US 12,377,064 B2
(45) Date of Patent: *Aug. 5, 2025

(54) TREATMENT OF MODERATE AND SEVERE GASTROPARESIS

(71) Applicant: EVOKE Pharma, Inc., Solana Beach, CA (US)

(72) Inventors: Marilyn R. Carlson, Encinitas, CA (US); Matthew J. D'Onofrio, Solana Beach, CA (US); David A. Gonyer, Cardiff, CA (US); Wayne Alves, Escondido, CA (US)

(73) Assignee: EVOKE PHARMA, INC., Solana Beach, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 18/047,364

(22) Filed: Oct. 18, 2022

(65) Prior Publication Data
US 2023/0094778 A1 Mar. 30, 2023

Related U.S. Application Data

(63) Continuation of application No. 16/469,092, filed as application No. PCT/US2017/066153 on Dec. 13, 2017, now Pat. No. 11,517,545.

(60) Provisional application No. 62/440,981, filed on Dec. 30, 2016, provisional application No. 62/435,044, filed on Dec. 15, 2016.

(51) Int. Cl.
| | |
|---|---|
| A61K 31/166 | (2006.01) |
| A61K 9/00 | (2006.01) |
| A61K 9/08 | (2006.01) |
| A61K 47/12 | (2006.01) |
| A61P 1/00 | (2006.01) |

(52) U.S. Cl.
CPC .......... *A61K 31/166* (2013.01); *A61K 9/0043* (2013.01); *A61K 9/08* (2013.01); *A61K 47/12* (2013.01); *A61P 1/00* (2018.01)

(58) Field of Classification Search
CPC ...... A61K 31/166; A61K 9/0043; A61K 9/08; A61K 47/12; A61P 1/00
See application file for complete search history.

(56) References Cited

U.S. PATENT DOCUMENTS

| | | | |
|---|---|---|---|
| 4,309,408 A | 1/1982 | Pathak et al. | |
| 4,624,965 A | 11/1986 | Wenig | |
| 4,729,997 A | 3/1988 | Wenig | |
| 5,116,857 A | 5/1992 | Acher et al. | |
| 5,576,317 A | 11/1996 | Gonsalves | |
| 5,578,632 A | 11/1996 | Tyers | |
| 5,624,677 A | 4/1997 | El-Rashidy et al. | |
| 5,760,086 A | 6/1998 | Psilogenis | |
| 5,780,431 A | 7/1998 | Ho et al. | |
| 5,854,269 A | 12/1998 | Haslwanter et al. | |
| 5,888,534 A | 3/1999 | El-Rashidy et al. | |
| 6,187,332 B1 | 2/2001 | Gern et al. | |
| 6,200,604 B1 | 3/2001 | Pather et al. | |
| 6,383,471 B1 | 5/2002 | Chen et al. | |
| 6,413,549 B2 | 7/2002 | Green et al. | |
| 6,419,094 B1 | 7/2002 | Zittel et al. | |
| 6,433,129 B1 | 8/2002 | Amendola et al. | |
| 6,572,891 B1 | 6/2003 | Ugarkovic | |
| 6,586,563 B1 | 7/2003 | Ortega et al. | |
| 6,770,262 B2 | 8/2004 | Lehman et al. | |
| 6,916,485 B2 | 7/2005 | Aiache et al. | |
| 6,974,590 B2 | 12/2005 | Pather et al. | |
| 7,122,198 B1 | 10/2006 | Singh et al. | |
| 7,651,698 B2 | 1/2010 | Aiache et al. | |
| 8,334,281 B2 | 12/2012 | D'Onofrio et al. | |
| 8,669,258 B2 | 3/2014 | Pasricha et al. | |
| 11,020,361 B2 | 6/2021 | D'Onofrio et al. | |
| 11,517,545 B2 * | 12/2022 | Carlson ..................... | A61P 1/00 |
| 11,628,150 B2 | 4/2023 | D'Onofrio et al. | |
| 11,813,231 B2 | 11/2023 | D'onofrio et al. | |
| 2001/0054581 A1 | 12/2001 | Bertolotti et al. | |
| 2002/0002175 A1 | 1/2002 | Behl et al. | |
| 2002/0065321 A1 * | 5/2002 | Lehman ..................... | A61P 1/14 |
| | | | 514/619 |
| 2002/0143030 A1 | 10/2002 | Cutler et al. | |
| 2003/0059374 A1 | 3/2003 | Lehman et al. | |
| 2003/0069232 A1 | 4/2003 | Chiou | |
| 2004/0192781 A1 | 9/2004 | Haley | |
| 2005/0137265 A1 | 6/2005 | Haley | |
| 2006/0069114 A1 | 3/2006 | Calderari et al. | |
| 2006/0127317 A1 | 6/2006 | Hesse et al. | |
| 2010/0163032 A1 | 7/2010 | D'Onofrio et al. | |

(Continued)

FOREIGN PATENT DOCUMENTS

| | | |
|---|---|---|
| EP | 0011489 A1 | 5/1980 |
| EP | 0911333 A1 | 4/1999 |

(Continued)

OTHER PUBLICATIONS

Ainge et al.: Lack of Deleterious Effects of Corticosteroid Sprays Containing Benzalkonium Chloride on Nasal Ciliated Epithelium Drug Investigation vol. 8, pp. 127-133 (1994).
Anda #71-340/R-10 Metoclopramide Oral Solution, USP 5 mg/5 ml. 21 pages (1992).
Bateman et al., The Pharmacokinetics of Metoclopramide in Man with Observations in the Dog, Br. J. Clin. Pharmac. 9:371-377 (1980).
Batts et al.: The Effect of Some preservatives used in nasal preparations on the mucus and ciliary component of mucocililary clearance. J. Pharm Pharmacol. 42:145-151 (1990).
Behl et al.: Effects of physicochemical properties and other factors on systemic nasal drug delivery. Advanced Drug Delivery. Reviews. 29:89-116 (1998).

(Continued)

*Primary Examiner* — James H Alstrum-Acevedo
*Assistant Examiner* — Justin Christopher Sanchez
(74) *Attorney, Agent, or Firm* — Mintz, Levin, Cohn, Ferris, Glovsky and Popeo, P.C.

(57) ABSTRACT

Metoclopramide is administered for the treatment of moderate to severe gastroparesis, in some embodiments, severe gastroparesis.

17 Claims, No Drawings

(56) References Cited

U.S. PATENT DOCUMENTS

| | | |
|---|---|---|
| 2013/0213393 A1 | 8/2013 | D'Onofrio et al. |
| 2013/0217775 A1 | 8/2013 | D'Onofrio et al. |
| 2017/0071885 A1 | 3/2017 | D'Onofrio et al. |
| 2019/0070134 A1 | 3/2019 | D'onofrio et al. |
| 2019/0328686 A1 | 10/2019 | Carlson et al. |
| 2019/0388370 A1 | 12/2019 | D'Onofrio et al. |
| 2020/0276139 A1 | 9/2020 | Carlson et al. |
| 2021/0093590 A1 | 4/2021 | D'onofrio et al. |
| 2021/0330618 A1 | 10/2021 | D'Onofrio et al. |
| 2021/0330619 A1 | 10/2021 | D'Onofrio et al. |
| 2021/0338608 A1 | 11/2021 | D'Onofrio et al. |
| 2022/0151960 A1 | 5/2022 | D'Onofrio et al. |
| 2023/0094778 A1 | 3/2023 | Carlson et al. |

FOREIGN PATENT DOCUMENTS

| | | |
|---|---|---|
| EP | 1097706 A1 | 5/2001 |
| HU | 210115 B | 2/1995 |
| JP | 2002356624 A | 12/2002 |
| JP | 2003506396 A | 2/2003 |
| JP | 2007522223 A | 8/2007 |
| JP | 2016516797 A | 6/2016 |
| JP | 2017532965 A | 11/2017 |
| WO | WO-9942095 A1 | 8/1999 |
| WO | WO-0174350 A1 | 10/2001 |
| WO | WO-2006036235 A2 | 4/2006 |
| WO | WO-2008096804 A1 | 8/2008 |
| WO | WO-2010075444 A2 | 7/2010 |
| WO | WO-2010109482 A2 | 9/2010 |
| WO | WO-2013028882 A1 | 2/2013 |
| WO | WO-2018112061 A1 | 6/2018 |
| WO | WO-2019051366 A1 | 3/2019 |
| WO | 2020180398 A1 | 9/2020 |
| WO | 2021146464 A1 | 7/2021 |

OTHER PUBLICATIONS

Bhise et al.: Bioavailability of intranasal drug delivery system Asian Journal of Pharmaceutics. Oct.-Dec. 2008, pp. 201 to 215.
Bortoli et al., Efficacy and tolerability of metoclopramide nasal spray in the symptomatic therapy of functional dyspepsia, Curr. Therapeutic Res. 55(10):1192-1200 (1994).
Camilleri et al.: Clinical Guideline: Management of Gastroparesis Am. J. Gastroenterol., 108(1):18-38 (2013).
Canadian Patent Application No. 2780485 First Examiner's report dated Nov. 20, 2015.
Canadian Patent Application No. 2780485 further Examiner's Report dated Jul. 19, 2016.
Canadian Patent Application No. 2,846,340 Office Action dated Apr. 24, 2018.
Canadian Patent Application No. 2,846,340 Office Action dated Mar. 11, 2021.
Canadian Patent Application No. 2,984,736 Examiner's Report dated Jul. 25, 2019.
Canadian Patent Application No. 2,984,736 Examiner's Report dated Nov. 5, 2018.
Center for Drug Evaluation and Research Application No. 75-051 Approved Draft Labeling. Metoclopramide Oral 17 pages (2001).
Chiara et al., Prevention of Delayed Emesis with Metoclopramide and Dexamethasone in Patients Receiving Moderately Emetogenic Cytotoxic Treatment, Anticancer Res. 15:1597-1599 (1995).
Citron et al.: Pharmacokinetic comparison of intranasal, oral, and intramuscular metoclopramide in healthy volunteers. Cancer Treat Rep. Mar. 1987;71(3):317-9.
Clark et al., Antiemetic (AE) trials to control delayed vomiting (V) following high-dose cisplatin (DDP), Proc. Of ASCO 5:257, abstract 1005 (1986).
Clark et al., Delayed emesis: A dilemma in antiemetic control, Support Care Cancer 1:182-185 (1993).
Costantino et al.: Intranasal delivery: physicochemical and therapeutic aspects Int J Pharm. Jun. 7, 2007;337(1-2):1-24.
Crinos Industria Pharmacobiologica S.p.A. package inserts for Pramidin 10 and Pramidin 20, Apr. 1999.
Cubeddu et al., Participation of serotonin on early and delayed emesis induced by initial and subsequent cycles of cisplatinum-based chemotherapy: Effects of antiemetics, J. Clin. Pharmacol. 33:691-697 (1993).
De Mulder et al., Ondansetron compared with high-dose metoclopramide in prophylaxis of acute and delayed cisplatin-induced nausea and vomiting, Ann. Internal Med. 113:834-840 (1990).
Desmond and Watson. Metoclopramide—a review The medical journal of Australia. Mar. 31, 1986, vol. 144 pp. 366-369.
Drenth and Engels, Diabetic gastroparesis. A critical reappraisal of new treatment strategies, Drugs 44:537-553 (1992).
Du Bois et al., Cisplatin-induced alterations of serotonin metabolism in patients with or without emesis following chemotherapy, Oncol. Rep. 2:839-842 (1995).
EP01922935.0 Supplementary Partial Search Report dated Jul. 13, 2007.
EP09835796.5 Office action dated Feb. 17, 2014.
EP09835796.5 Supplementary European Search Report dated Apr. 25, 2012.
EP12825447.1 Extended European Search Report dated Nov. 20, 2014.
EP17881606.2 Extended European Search Report dated May 15, 2020.
EP97915060.4 Supplementary Search Report dated Jan. 23, 2004.
Erbas et al., Comparison of metoclopramide and erythromycin in the treatment of diabetic gastroparesis. Diabetes Care. 16:1511-1514 (1993).
European Patent Application No. 12825447.1 Communication dated Feb. 14, 2017.
European Patent Application No. 12825447.1 Communication dated Sep. 8, 2017.
European Patent Application No. 12 825 447.1 Communication dated Nov. 10, 2015.
*Evoke Pharma, Inc. v. Teva Pharmaceuticals Inc.* Case 1:22-cv-02019-RMB-SAK12645108 Apr. 11, 2022.
*Evoke Pharma, Inc. v. Teva Pharmaceuticals Inc.* Case 1:22-cv-02019-RMB-SAK16181841 Apr. 8, 2022.
FDA: Center for Drug Evaluation and Research. Center for Biologics Evaluation and Research. Q1A(R2) Stability Testing of New Drug Substances and Products 25 pages. Nov. 2003.
Gandara et al., The delayed-emesis syndrome from cisplatin: Phase III evaluation of ondansetron versus placebo, Semin. Oncol. 19:67-71 (1992).
Gangula et al. Diabetes Induces Sex-dependent Changes in Neuronal Nitric Oxide Synthase Dimerization and Function in the Rat GastricAntrum. Am J Physiol Gastrintest, 292(3):G725-G733 (2007).
Gangula et al. Gender Bias in Gastroparesis: Is Nitric Oxide the Answer? Dig Dis Sci 56(9):2520-2527 (2011).
Grabnar et al.: Bioavailability of metoclopramide from a new chewing gum device Journal of Drug Delivery Science and Technology. vol. 17, Issue 3, 2007, pp. 173-176.
Gralla et al., The management of chemotherapy-induced Nausea and Vomiting, Medical Clinics of North America (Cancer Pain) 71:289-301 (1987).
Grobuschek et al.: Mass uniformity of nasal sprays. Scientia Pharmaceutica. 2003; 71(3):151-164.
Grunberg et al., Oral metoclopramide with or without diphenhydramine: Potential for prevention of late nausea and vomiting induced by cisplatin, J. Natl. Cancer Inst. 80:864-868 (1988).
Guidance for Industry on Patient-Reported Outcome Measures: Use in Medical Product Development to Support Labeling Claims; Availability. Federal Register, 74(235), Dec. 9, 2009, p. 65132.
Guidance for Industry Patient-Reported Outcome Measures: Use in Medical Product Development to Support Labeling Claims U.S. Department of Health and Human Services, Dec. 2009, p. 1-43.
Hasler, Factors related to abdominal pain in gastroparesis: Contrast to patients with predominant nausea and vomiting Neurogastroenterol Motil., 25(5):427-e301 (2013).
Hoogerwerf et al., Pain: The overlooked symptom in gastroparesis The American Journal of Gastro., 94(4):1-5 (1999).
Hospira, Inc. Metoclopramide Injection, USP. 5 pages (2007).

(56) References Cited

OTHER PUBLICATIONS

Human Weight from Wikipedia Jun. 7, 2007, pp. 1-2, http://en.wikipedia.org/wiki/Human_weight.
International Application No. PCT/US2018/050191 International Search Report and Written Opinion dated Dec. 13, 2018.
Italian Official Gazette. Marketing authorization of the medicinal product for human use. p. 68 (1999).
Jones et al., Comparison of dexamethasone and ondansetron in the prophylaxis of emesis induced by moderately emetogenic chemotherapy, Lancet 338:483-486 (1991).
Jung et al., The incidence, prevalence and outcomes of patients with gastroparesis in Olmsted County, Minnesota from 1996-2006 Gastroenterology, 136(4):1225-1233 (2009).
Kenney et al. Metoclopramide, an Increasingly Recognized Cause of Tardive Dyskinesia. Journ Clin Pharma 48:379-384 (2008).
Kris et al., Controlling delayed vomiting: Double-blind, randomized trial comparing placebo, dexamethasone alone, and metoclopramide plus dexamethasone in patients receiving cisplatin, J. Clin. Oncol. 7:108-114 (1989).
Kris et al., Oral ondansetron for the control of delayed emesis after cisplatin, Cancer Suppl. 70:1012-1016 (1992).
Kupper et al.: Drugs and drug administration in extreme environments J Travel Med. Jan.-Feb. 2006;13(1):35-47.
Lee et al., Ondansetron compared with ondansetron plus metoclopramide in the prevention of cisplatin-induced emesis, J. Korean Med. Sci. 9:369-375 (1994).
Lee et al., Metoclopramide in the treatment of diabetic gastroparesis. Expert Rev Endocrinol Metab. 5(5):653-662 (2010).
Levitt et al., Ondansetron compared with dexamethasone and metoclopramide as antiemetics in the chemotherapy of breast cancer with cyclophosphamide, methotrexate, and fluorouracil, New Eng. J. Med. 328:1081-1084 (1993).
Li et al.,: Control of cisplatin-induced delayed emesis, Chin. Med. J. (Taipei) 48:451-455 (1991).
Locatelli et al., Tolerability and Safety of Nasally Administered Metoclopramide (MCP) for the Prevention of CIS-Platinum (CDDP) induced Delayed Emesis, Proc. ASCO vol. Mar. 14, 1995, abstr. 1759.
Longo, W.S., and Vernava, A.M., Prokinetic Agents for Lower Gastrointestinal Motility Disorders, Dis Colon Rectum 36:696-708 (1993).
Longstreth et al., Metoclopramide stimulation of gastric motility and emptying in diabetic gastroparesis. Ann Intern Med.86:195-196 (1977).
Loo et al., Gastric emptying in patients with diabetes mellitus. Gastroenterology. 86:485-494 (1984).
Madej et al., A report comparing the use of tropisetron (Navoban), a 5-HT, antagonist, with a standard antiemetic regimen of dexamethasone and metoclopramide in cisplatin-treated patients under conditions of severe emesis, Semin. Oncol. 21:3-6 (1994).
Malfertheiner, Current concepts in dyspepsia: A world perspective, Eur. J. Gastroenterol. Hepatol. 1(Suppl. 1):S25-S29 (1999).
Maquille et al.: Radiosterilization of drugs in aqueous solutions may be achieved by the use of radioprotective excipients. International journal of pharmaceutics. 349(1-2):74-82 (2008).
McCallum et al., A multicenter placebo controlled clinical trial of oral metoclopramide in diabetic gastroparesis. Diabetes Care.6:463-467 (1983).
McCallum et al.: Evoke Symptom Severity Influences Drug Efficacy in Women with Diabetic Gastroparesis: Results of a Phase 3 Study with Metoclopramide Nasal Spray. XP055688742 https://evokepharmainc.gcs-web.com/static-files/533ae809-538d-4a5d-9633-ce17349b7819 (2020).
Mearin et al., Placebo in Functional Dyspepsia: Symptomatic, Gastrointestinal Motor, and Gastric Sensorial Responses, Am. J. Gastroenterol. 94(1):116-125 (1999).
Metoclopramide Oral Monograph from Medscape Oct. 23, 2009, 2 pages.
Metoclopramide Prescribing Information (PI), FDA approved Jan. 26, 2001.

Metozolv (metoclopramide hydrochloride) Orally Disintegrating Tablets. Summary Review (2009).
Mohan. Calbiochem Buffers. published by EMD. pp. 1-33 (2006).
Moreno et al., Comparison of three protracted antiemetic regimens for the control of delayed emesis in cisplatin-treated patients, Eur. J. Cancer 28:1344-1347 (1992).
Mullin and Beckwith Prevention and Management of Chemotherapy-Induced Nausea and Vomiting, Part 2 Hospital Pharmacy. 2001;36(3):280-308.
Musunuru et al., Preoperative predictors of significant symptomatic response after 1 year of gastric electrical stimulation for Gastroparesis. World J. Surgery, 34:1853-1858, 2010.
Navari et al., Oral ondansetron for the control of cisplatin-induced delayed nemesis: A large, multicenter, double-blind, randomized comparative trial of ondansetron versus placebo, J. Clin. Oncol. 13:2408-2416 (1995).
Nino et al., A randomized controlled trial of acute and delayed cisplatin-induced emesis with metoclopramide, dexamethasone and prochlorperazine, Jpn. J. Cancer Chemother. 14:2861-2884 (1987).
O'Brien et al., The role of metoclopramide in acute and delayed chemotherapy induced emesis: A randomized double blind trial, Br. J. Cancer 60:759-763 (1989).
Ogawa, Metoclopramide as an antiemetic in chemotherapy, New Eng. J. Med. Correspond. 307:249-250 (1982).
Ohwaki et al.: Effects of dose, pH, and osmolarity on nasal absorption of secretin in rats. II: Histological aspects of the nasal mucosa in relation to the absorption variation due to the effects of pH and osmolarity J Pharm Sci. Sep. 1987;76(9):695-8.
Ohwaki et al.: Effects of dose, pH, and osmolarity on nasal absorption of secretin in rats. J Pharm Sci. May 1985;74(5):550-2.
Ormrod and Goa, Intranasal Metoclopramide, reprinted from Drugs 58(2):315-324 (1999).
Parkman et al., Clinical, demographic, and pharmacogenetics associations with the clinical response and side effects to metoclopramide, Gastroenterology, 140(5) Supplement 1:S24, 2011.
Parkman et al., Gastroparesis and functional Dyspepsia: Excerpts from the AGA/ANMS Meeting Neurogastroenterol Motil., 22(2):113-133 (2010).
Parkman et al., Metoclopramide nasal spray is effective in symptoms of gastroparesis in diabetics compared to conventional oral tablet Neurogastroenterology & Motility, 26(4): 521-528 (2014).
Parkman et al. Metoclopramide Nasal Spray Reduces Symptoms of Gastroparesis in Women, But Not Men, With Diabetes: Results of a Phase 2B Randomized Study. Clin Gastro Hepa 13:1256-1263 (2015).
Pasricha et al. Drug Insight: From Disturbed Motility to Disordered Movement—A Review of the Clinical Benefits and Medicolegal Risks of Metoclopramide. Nature Clin Practice 3(3):138-148 (2006).
Pasricha et al., Outcomes and factors associated with reduced symptoms in patients with Gastroparesis Gastroenterology, 149:1762-1774 (2015).
Patterson et al., A double-blind multicenter comparison of domperidone and metoclopramide in the treatment of diabetic patients with symptoms of gastroparesis. Am J Gastroenterol. 94:1230-1234 (1999).
PCT/US09/69298 International Preliminary Report on Patentability dated Jun. 29, 2011.
PCT/US09/69298 Search Report and Written Opinion dated Sep. 3, 2010.
PCT/US12/52096 International Search Report and Written Opinion mailed Oct. 23, 2012.
PCT/US2001/10356 Search Report dated Jun. 13, 2001.
PCT/US2017/066153 International Search Report and Written Opinion dated Mar. 1, 2018.
PCT/US97/03974 Search Report dated Jun. 25, 1997.
Perkel et al., Metoclopramide therapy in patients with delayed gastric emptying: a randomized, double-blind study. Dig Dis Sci. 24:662-666 (1979).
Perkel, M.S. et al., Metoclopramide Therapy in Fifty-five Patients With Delayed Gastric Emptying, Am. J. Gastroenterol. 74:231-236 (1980).
Pramidin Prescribing Information (PI) (1997).

(56) References Cited

OTHER PUBLICATIONS

Press Release. Evoke completes Phase 3 clinical trial of EVK-001 in women with symptoms associated with diabetic gastroparesis. Jun. 1, 2016, 2 pages.
Press Release. Evoke Pharma announces positive non-clinical pre-NDA meeting with FDA for Gimoti. Sep. 7, 2016, 1 page.
Press Release. Evoke Pharma reports topline results from EVK-001 Phase 3 clinical trial. Jul. 18, 2016, 1 page.
Press Release. Evoke receives positive NDA submission guidance from US FDA for Gimoti. Dec. 15, 2016, 2 pages.
Press Release, Evoke provides additional data demonstrating statistically significant benefit for Gimoti in moderate to severe patients in Phase 3 Diabetic Gastroparesis trial. Jan. 4, 2017, 2 pages.
Pujara et al.: Effects of formulation variables on nasal epithelial cell integrity: biochemical evaluations. Int. J. Pharm. 114:197-203 (1995).
Ravella et al. Chronic Estrogen Deficiency Causes Gastroparesis by Altering Neuronal Nitric Oxide Synthase Function. Dig Dis Sci 58(6):1507-1515 (2013).
Reddymasu and McCALLUM, Pharmacotherapy of gastroparesis. Expert Opinion, 10(3):469-484, 2009.
Reglan Injection Label (metoclopramide injection, USP) (2010).
Reglan ODT Label dated Nov. 2011.
Reglan Tablets (A.H. Robins) Dec. 30, 1980 Approval (Diabetic Gastroparesis): Approval Letter; Final Labeling; Summary Basis of Approval; Medical Officers Review; Pharmacology/Toxicology; Chemistry; Bioavailability/Dissolution. Provided by FOI Services, Inc., Gaithersburg, MD, No. 5234543 E, 236 pages.
Reglan Tablets (Metoclopramide tablets, USP) Rx Only, Label Description, 18 pages; dated Aug. 2011.
Reglan® Tablets. Physicians' Desk Reference, PDR® 54th edition 2000, p. 2603-2605.
Remington's Pharmaceutical Sciences, Entries for stability testing, metoclopramide hydrochloride, and nasal solutions, pp. 257, 809, 1500 (1985).
Rentz et al., Development and psychometric evaluation of the patient assessment of upper gastrointestinal symptom severity index (PAGI-SYM) in patients with upper gastrointestinal disorders Quality of Life Research, 13:1737-1749 (2004).
Revicki et al., Development and content validity of a gastroparesis cardinal symptom index daily diary Alimentary Pharmacology & Therapeutics, 30:670-680 (2009).
Revicki et al., Development and validation of a patient-assesses gastroparesis symptom severity measure: the Gastroparesis Cardinal Symptom Index Ailment Pharmacol. Ther., 18:141-150 (2003).
Revicki et al., Evaluating symptom outcomes in gastroparesis clinical trials: validity and responsiveness of the Gastroparesis Cardinal Symptom Index-Daily Diary (GCSI-DD) Neurogastroenterology & Motility, 24:456-e216 (2012).
Revicki et al., Gastroparesis cardinal symptom index (GCSI): Development and validation of a patient reported assessment of severity of gastroparesis symptoms Quality of Life Research, 13:833-844 (2004).
Ricci et al., Effect of metoclopramide in diabetic gastroparesis. J Clin Gastroenterol. 7:25-32 (1985).
Roila et al., Cisplatin-induced delayed emesis: Pattern and prognostic factors during three subsequent cycles, Ann. Oncol. 5:585-589 (1994).
Roila et al., Predictive factors of delayed emesis in cisplatin-treated patients and antiemetic activity and tolerability of metoclopramide or dexamethasone, Am. J. Clin. Oncol. (CCT) 14: 238-242 (1991).
Scaglione et al., Pharmacokinetics and bioavailability of metoclopramide nasal spray versus metoclopramide intravenous in healthy volunteers and cancer patients, Arzneim.-Forsch./Drug Res. 43:986-988 (1993).
Shinkai et al., Control of Cisplatin-induced Delayed Emesis with Metoclopramide and Dexamethasone: A Randomized Controlled Trial, Jpn. J. Clin. Oncol. 19:40-44 (1989).
Snape et al., Metoclopramide to treat gastroparesis due to diabetes mellitus: a double-blind, controlled trial. Ann Intern Med.96:444-446 (1982).
Soukop et al., Ondansetron compared with metoclopramide in the control of emesis and quality of life during repeated chemotherapy for breast cancer, Oncol. 49:295-304 (1992).
Soykan et al. Demography, Clinical Characteristics, Psychological and Abuse Profiles, Treatment and Long-Term Follow-up of Patients with Gastroparesis. Dig Dis Sci 43(11):2398-2404 (1998).
Spiegel et al., Clinical determinants of health-related quality of life in patients with irritable bowel syndrome Arch. Intern. Med., 164:1773-1780 (2004).
Stanghellini and Corinaldesi, Relevance of gastrointestinal motor disturbances in functional dyspepsia, Bailliere's Clinical Gastroenterology 12(3):533-544 (1998).
Steeves et al., Effects of metoclopramide on the pharmacokinetics of a slow-release theophylline product. Clinical Pharmacy, 1(4):356-360, 1982.
Strum et al., Management of cisplatin (DDP)-induced delayed-onset nausea (N) and vomiting (V): Preliminary results with 2 drug regimens, Proc. ASCO 4:263, abstr. C-1024 (1985).
Suleiman et al.: Stability-indicating high-performance liquid chromatographic assay for the determination of metoclopramide hydrochloride in pharmaceutical dosage forms. Analyst. Mar. 1989; 114(3):365-8.
Tas et al.: Nasal absorption of metoclopramide from different Carbopol 981 based formulations: In vitro, ex vivo and in vivo evaluation Eur J Pharm Biopharm. Oct. 2006;64(2):246-54.
Taylor et al., Oral Bioavailability of High-Dose Metoclopramide, Eur. J. Clin. Pharmacol. 31:41-44 (1986).
Tomirotti et al., Efficacy and tolerability of nasally administered compared to parenterally administered metoclopramide in the symptomatic treatment of chemotherapy-induced emesis in cancer outpatients, Support Care Cancer 2:389-392 (1994).
United States Pharmacopeia (USP) 32 National Formulary (NF) 27 631 Color and Achromicity (3 pages) 2009.
United States Pharmacopeia (USP) 32 National Formulary (NF) 27 851 Spectrophotometry and Light Scattering. 7 pages (2009).
United States Pharmacopeia (USP) 37 National Formulary (NF) 27 1061 Color—Instrumental Measurement. 4 pages (2009).
U.S. Appl. No. 13/593,215 Office Action mailed Dec. 18, 2014.
U.S. Appl. No. 13/660,709 Office action mailed Aug. 28, 2014.
U.S. Appl. No. 13/660,709 Office Action mailed Mar. 17, 2015.
U.S. Appl. No. 16/469,092 Final Office Action dated Aug. 5, 2022.
U.S. Appl. No. 17/100,664 Final Office Action dated Oct. 4, 2022.
U.S. Appl. No. 13/593,215 Office Action dated Dec. 26, 2017.
U.S. Appl. No. 13/593,215 Office Action dated Feb. 25, 2016.
U.S. Appl. No. 13/593,215 Office Action dated May 23, 2017.
U.S. Appl. No. 13/593,215 Office Action dated Sep. 9, 2016.
U.S. Appl. No. 15/130,086 Office Action dated Aug. 17, 2017.
U.S. Appl. No. 15/130,086 Office Action dated May 14, 2018.
U.S. Appl. No. 16/016,246 Final Office Action dated Jan. 29, 2021.
U.S. Appl. No. 16/016,246 Office Action dated Feb. 21, 2020.
U.S. Appl. No. 16/181,841 Final Office Action dated Feb. 2, 2021.
U.S. Appl. No. 16/181,841 Office Action dated Apr. 24, 2020.
U.S. Appl. No. 16/469,092 Office Action dated Feb. 3, 2022.
U.S. Appl. No. 16/646,527 Final Office Action dated Jun. 20, 2022.
U.S. Appl. No. 16/646,527 Office Action dated Mar. 3, 2022.
U.S. Appl. No. 17/100,664 Final Office Action dated May 26, 2021.
U.S. Appl. No. 17/100,664 Office Action dated Mar. 15, 2021.
U.S. Appl. No. 17/100,664 Office Action dated May 11, 2022.
U.S. Appl. No. 17/100,664 Restriction Requirement dated Feb. 2, 2021.
U.S. Appl. No. 17/366,829 Final Office Action dated Jun. 29, 2023.
U.S. Appl. No. 17/366,829 Office Action dated Mar. 14, 2022.
U.S. Appl. No. 17/366,829 Office Action dated Nov. 7, 2022.
U.S. Appl. No. 17/366,829 Office Action dated Oct. 5, 2021.
U.S. Appl. No. 17/366,829 Restriction Requirement dated Aug. 12, 2021.
U.S. Appl. No. 16/469,092 Restriction Requirement dated May 20, 2021.
Vivien et al., Nasal Absorption of Metoclopramide Administered to Man, Eur. J. Pharmaceutics and Biopharmaceutics 40(4):228-231 (1994).

(56) References Cited

OTHER PUBLICATIONS

Vogt et al., Oral Medium-Dosed Metoclopramide versus Placebo as Highly Effective Antiemetic Prophylaxis in In-and-Outpatients on Noncisplatin Chemotherapy, Oncol. 50:81-85 (1993).
Ward et al.: Bioavailability of intranasal metoclopramide. Br J Clin Pharmacol. Nov. 1989;28(5):616-8.
Wo et al. Motility and Functional Disorders of the stomach: Diagnosis and Management of Functional Dyspepsia and Gastroparesis. Practical Gastroenterology, 2006, GI Motility, A Series from the AMS, Series # 4, p. 23-48.
Zaki et al.: Rapid-onset intranasal delivery of metoclopramide hydrochloride. Part I. Influence of formulation variables on drug absorption in anesthetized rats. International Journal of Pharmaceutics, Jul. 25, 2006, 327(1-2):89-96.
Office Action issued in Chinese Patent Application No. 201280052214.2 mailed on Jan. 16, 2017.
Office Action issued in Chinese Patent Application No. 201280052214.2 mailed on Sep. 8, 2017.
Office Action issued in Chinese Patent Application No. 201280052214.2 mailed on Mar. 18, 2015.
Office Action issued in Chinese Patent Application No. 201280052214.2 mailed on Feb. 2, 2016.
Office Action issued in Chinese Patent Application No. 201280052214.2 mailed on Jul. 5, 2016.
Gandara (1991) "Progress in the Control of Acute and Delayed Emesis Induced by Cisplatin", European Journal of Cancer, 27:S9-S11.
"Highlights of Prescribing Information Reglan ODT", 1-10. (15 Pages).
Office Action issued in Japanese Patent Application No. 2014-527302 mailed on Apr. 3, 2017.
Office Action issued in Japanese Patent Application No. 2014-527302 mailed on Jun. 29, 2016.
Office Action issued in Japanese Patent Application No. 2014-527302 mailed on Jun. 4, 2018.
Office Action issued in Japanese Patent Application No. 2017-145855 mailed on Dec. 19, 2018.
Office Action issued in Japanese Patent Application No. 2017-145855 mailed on Jun. 11, 2018.
Office Action issued in Japanese Patent Application No. 2018-203340 mailed on Jan. 10, 2019.
Office Action issued in Japanese Patent Application No. 2018-203340 mailed on Sep. 11, 2019.
Notice of Allowance issued in Mexican Patent Application No. Mx/a/2014/002125 mailed on Mar. 22, 2018.
Medical Economics Co. (1999), PDR 53th Ed., "Physician's Desk Refernce" 2643-2645.
Official Action issued in Mexican Patent Application No. MX/a/2014/002125 mailed on Nov. 13, 2015.
Office action issued in Mexican Patent Application No. MX/a/2014/002125 mailed on Feb. 17, 2017.
Office Action issued in Mexican Patent Application No. Mx/a/2017/015559 mailed on Mar. 20, 2019.
Office Action issued in Mexican Patent Application No. MX/a/2014/002125 mailed on Jul. 28, 2017.
Office Action issued in Russian Patent Application No. 2014111070 mailed on Jul. 13, 2016.
Robins (1999) "Product Information on Reglan", obtained from on-line PDR, 2642-2645.

* cited by examiner

TREATMENT OF MODERATE AND SEVERE GASTROPARESIS

CROSS REFERENCE

This application is a Continuation of U.S. patent application Ser. No. 16/469,092, filed on Jun. 12, 2019, which is a National Stage Entry of International Application No. PCT/US2017/066153, which claims the benefit of U.S. Provisional Application No. 62/435,044, filed on Dec. 15, 2016 and U.S. Provisional Application No. 62/440,981, filed on Dec. 30, 2016, all of which are incorporated herein by reference in their entireties.

BACKGROUND OF THE INVENTION

Metoclopramide is approved in the United States in oral solution, oral tablet, orally dissolving tablet and injectable solution forms. Wenig has suggested the use of nasally-administered metoclopramide for the treatment of emesis or nausea. (See U.S. Pat. No. 4,624,965, issued Nov. 25, 1986, which is incorporated by reference herein in its entirety.) Psilogenis has suggested nasal administration of metoclopramide for the treatment of delayed onset emesis. (See U.S. Pat. No. 5,760,086, issued Jun. 2, 1998, incorporated herein by reference in its entirety.) Lehman et al. have proposed administering nasal formulations of metoclopramide for the treatment of gastroparesis. (See U.S. Pat. No. 6,770,262, issued Aug. 3, 2004, incorporated herein by reference in its entirety.)

SUMMARY OF THE INVENTION

At the direction of the inventors, a clinical study of the efficacy of intranasal metoclopramide was carried out in women who had been diagnosed as having gastroparesis. The clinical study data showed statistically significant efficacy compared to placebo for patients with moderate to severe symptoms at baseline.

Some embodiments described herein relate to a method of treating moderate to severe gastroparesis in a human, comprising intranasally administering to a human an amount of metoclopramide, or a pharmaceutically acceptable salt thereof, effective to treat moderate to severe gastroparesis. In some embodiments, the human is a human gastroparesis patient; and the human gastroparesis patient is a human who has been diagnosed with, or is suspected of suffering from, gastroparesis. In some embodiments, the human gastroparesis patient is an adult. In some embodiments, the human gastroparesis patient is either a female or a male. In some embodiments, the human gastroparesis patient is a member of a treatment group consisting of both female humans and male humans. In some embodiments, the human gastroparesis patient is a member of a treatment group consisting of female humans, and excluding all male humans. In some embodiments the human gastroparesis patient is diabetic, such as a human female diabetic patient. In some embodiments, the administered amount is ineffective to treat mild gastroparesis in female humans. In some embodiments, the effective amount of metoclopramide is ineffective to treat symptoms associated with gastroparesis in males. In some embodiments, a predefined treatment group is established, which includes only females and excludes all males. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some particular embodiments, the intranasal aliquots are roughly equal. In some embodiments, each intranasal aliquot has a volume of about 25 µL to 150 µL. In some embodiments, each intranasal aliquot has a volume of about 50 µL. In some embodiments, the daily dose of metoclopramide is administered as 3-8 aliquots of about 14 mg metoclopramide base per aliquot. In some embodiments, each aliquot has a volume of approximately 25 µL to 150 µL. In some embodiments, each aliquot has a volume of approximately 70 µL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 µL to 150 µL. In some embodiments, the treatment of moderate to severe gastroparesis includes treatment of moderate to severe diabetic gastroparesis.

Some embodiments described herein relate to a method of treating moderate to severe gastroparesis in a human treatment group, comprising intranasally administering to members of the human treatment group an amount of metoclopramide, or a pharmaceutically acceptable salt thereof, effective to treat moderate to severe gastroparesis. In some embodiments, the human treatment group consists of human gastroparesis patients; and the human gastroparesis group are humans who have been diagnosed with, or are suspected of suffering from, gastroparesis. In some embodiments, the humans are adults. In some embodiments, the human treatment group is a female human treatment group, which consists of only females and excludes all males. In some embodiments the human treatment group comprises diabetic patients, such as a human female diabetic patients. In some embodiments, the administered amount is ineffective to treat mild gastroparesis in female humans. In some embodiments, the treatment group excludes patients diagnosed with, or suspected of having, mild gastroparesis. In some embodiments, the treatment group excludes all male patients and female patients diagnosed with, or suspected of having, mild gastroparesis. In some embodiments, a predefined treatment group is established, which includes only females and excludes all males. In some embodiments, a predefined treatment group is established, which includes only patients diagnosed with, or suspected of having, moderate to severe gastroparesis, and excludes all patients diagnosed with, or suspected of having, mild gastroparesis. In some embodiments, a predefined treatment group is established, which includes only females diagnosed with, or suspected of having, moderate to severe gastroparesis, specifically excludes all females diagnosed with, or suspected of having, mild gastroparesis, and specifically excludes all males. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some particular embodiments, the intranasal aliquots are roughly equal. In some embodiments, each intranasal aliquot has a volume of about 25 μL to 150 μL. In some embodiments, each intranasal aliquot has a volume of about 50 μL. In some embodiments, the daily dose of metoclopramide is administered as 3-8 aliquots of about 14 mg metoclopramide base per aliquot. In some embodiments, each aliquot has a volume of approximately 25 ∞L to 150 μL. In some embodiments, each aliquot has a volume of approximately 70 μL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 μL to 150 μL. In some embodiments, the treatment of moderate to severe gastroparesis includes treatment of moderate to severe diabetic gastroparesis.

Some embodiments described herein relate to a method of treating moderate to severe female gastroparesis, comprising administering to a human female an effective amount of metoclopramide or a pharmaceutically acceptable salt thereof. In some embodiments, the administration of metoclopramide is oral, buccal, sublingual, intranasal, pulmonary, topical, transdermal, rectal or intravenous administration of metoclopramide to a human female. In some preferred embodiments the administration of metoclopramide is intranasal administration to a human female. The effective amount of metoclopramide is ineffective to treat symptoms associated with male gastroparesis. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some particular embodiments, the intranasal aliquots are roughly equal. In some embodiments, each intranasal aliquot has a volume of about 25 μL to 150 μL. In some embodiments, each intranasal aliquot has a volume of about 50 μL. In some embodiments, the daily dose of metoclopramide is administered as 3-8 aliquots of about 14 mg metoclopramide base per aliquot. In some embodiments, each aliquot has a volume of approximately 25 μL to 150 μL. In some embodiments, each aliquot has a volume of approximately 70 μL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 μL to 150 μL. In some embodiments, the treatment of moderate to severe female gastroparesis includes treatment of moderate to severe female diabetic gastroparesis.

Some embodiments described herein relate to a composition for the treatment of moderate to severe gastroparesis, such as moderate to severe female gastroparesis, said treatment comprising administering to a human female an effective amount of metoclopramide or a pharmaceutically acceptable salt thereof. In some embodiments, the administration of metoclopramide is oral, buccal, sublingual, intranasal, pulmonary, topical, transdermal, rectal or intravenous. In some preferred embodiments, the administration of metoclopramide is intranasal. In some embodiments, the amount of administered metoclopramide is ineffective to treat mild gastroparesis. In some embodiments, the effective amount of intranasal metoclopramide is ineffective to treat symptoms associated with male gastroparesis. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some embodiments, each intranasal aliquot has a volume of about 25 μL to 150 μL. In some embodiments, each intranasal aliquot has a volume of about 50 μL. In some embodiments, the daily dose of metoclopramide is administered as 3-8 aliquots of about 14 mg metoclopramide base per aliquot. In some embodiments, each aliquot has a volume of approximately 25 μL to 150 μL. In some embodiments, each aliquot has a volume of approximately 70 μL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 μL to 150 μL. In some embodiments, the treatment of moderate to severe female gastroparesis includes treatment of moderate to severe female diabetic gastroparesis. Some embodiments provide for use of a composition described herein for the preparation of a medicament for the treatment of moderate to severe female gastroparesis, such as moderate to severe female diabetic gastroparesis.

Some embodiments described herein relate to a method of treating severe gastroparesis in a human, comprising intranasally administering to a human an amount of metoclopramide, or a pharmaceutically acceptable salt thereof, effective to treat severe gastroparesis. In some embodiments, the human is a human gastroparesis patient; and the human gastroparesis patient is a human who has been diagnosed with, or is suspected of suffering from, gastroparesis. In some embodiments, the human gastroparesis patient is an adult. In some embodiments, the human gastroparesis patient is a member of a treatment group consisting of female humans, and excluding all male humans. In some embodiments the human gastroparesis patient is diabetic, such as a human female diabetic patient. In some embodiments, the administered amount is ineffective to treat mild gastroparesis in female humans. In some embodiments, the effective amount of metoclopramide is ineffective to treat symptoms associated with gastroparesis in males. In some embodiments, a predefined treatment group is established, which includes only females and excludes all males. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some particular embodiments, the intranasal aliquots are roughly equal. In some embodiments, each intranasal aliquot has a volume of about 25 µL to 150 µL. In some embodiments, each intranasal aliquot has a volume of about 50 µL. In some embodiments, the daily dose of metoclopramide is administered as 3-8 aliquots of about 14 mg metoclopramide base per aliquot. In some embodiments, each aliquot has a volume of approximately 25 µL to 150 µL. In some embodiments, each aliquot has a volume of approximately 70 µL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 µL to 150 µL. In some embodiments, the treatment of severe gastroparesis includes treatment of severe diabetic gastroparesis.

Some embodiments described herein relate to a method of treating severe gastroparesis in a human treatment group, comprising intranasally administering to members of the human treatment group an amount of metoclopramide, or a pharmaceutically acceptable salt thereof, effective to treat severe gastroparesis. In some embodiments, the human treatment group consists of human gastroparesis patients; and the human gastroparesis group are humans who have been diagnosed with, or are suspected of suffering from, gastroparesis. In some embodiments, the humans are adults. In some embodiments, the human treatment group is a female human treatment group, which consists of only females and excludes all males. In some embodiments the human treatment group comprises diabetic patients, such as a human female diabetic patients. In some embodiments, the administered amount is ineffective to treat mild gastroparesis in female humans. In some embodiments, the treatment group excludes patients diagnosed with, or suspected of having, mild gastroparesis. In some embodiments, the treatment group excludes all male patients and female patients diagnosed with, or suspected of having, mild gastroparesis. In some embodiments, a predefined treatment group is established, which includes only females and excludes all males. In some embodiments, a predefined treatment group is established, which includes only patients diagnosed with, or suspected of having, severe gastroparesis, and excludes all patients diagnosed with, or suspected of having, mild gastroparesis. In some embodiments, a predefined treatment group is established, which includes only females diagnosed with, or suspected of having, severe gastroparesis, specifically excludes all females diagnosed with, or suspected of having, mild gastroparesis, and specifically excludes all males. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some particular embodiments, the intranasal aliquots are roughly equal. In some embodiments, each intranasal aliquot has a volume of about 25 µL to 150 µL. In some embodiments, each intranasal aliquot has a volume of about 50 µL. In some embodiments, the daily dose of metoclopramide is administered as 3-8 aliquots of about 14 mg metoclopramide base per aliquot. In some embodiments, each aliquot has a volume of approximately 25 µL to 150 µL. In some embodiments, each aliquot has a volume of approximately 70 µL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 µL to 150 µL. In some embodiments, the treatment of severe gastroparesis includes treatment of severe diabetic gastroparesis.

Some embodiments described herein relate to a method of treating severe female gastroparesis, comprising administering to a human female an effective amount of metoclopramide or a pharmaceutically acceptable salt thereof. In some embodiments, the administration of metoclopramide is oral, buccal, sublingual, intranasal, pulmonary, topical, transdermal, rectal or intravenous administration of metoclopramide to a human female. In some preferred embodiments the administration of metoclopramide is intranasal administration to a human female. The effective amount of metoclopramide is ineffective to treat symptoms associated with male gastroparesis. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some particular embodiments, the intranasal aliquots are roughly equal. In some embodiments, each intranasal aliquot has a volume of about 25 µL to 150 µL. In some embodiments, each intranasal aliquot has a volume of about 50 µL. In some embodiments, the daily dose of metoclopramide is administered as 3-8 aliquots of about 14 mg metoclopramide base per aliquot. In some embodiments, each aliquot has a volume of approximately 25 µL to 150 µL. In some embodiments, each aliquot has a volume of approximately 70 µL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 µL to 150 µL. In some embodiments, the treatment of severe female gastroparesis includes treatment of severe female diabetic gastroparesis.

Some embodiments described herein relate to a composition for the treatment of severe gastroparesis, such as severe female gastroparesis, said treatment comprising administering to a human, e.g. a human female, an amount of metoclopramide or a pharmaceutically acceptable salt thereof, effective to treat severe gastroparesis, such as severe female gastroparesis. In some embodiments, the administration of metoclopramide is oral, buccal, sublingual, intranasal, pulmonary, topical, transdermal, rectal or intravenous. In some preferred embodiments, the administration of metoclopramide is intranasal. In some embodiments, the amount of administered metoclopramide is ineffective to treat mild gastroparesis. In some embodiments, the effective amount of intranasal metoclopramide is ineffective to treat symptoms associated with male gastroparesis. In some embodiments, the metoclopramide is administered at a daily dose of approximately 20 mg to 160 mg (e.g., 40 mg to 80 mg) of metoclopramide base per day. In some embodiments, the daily dose of metoclopramide is administered as 1 to 8 intranasal aliquots. In some embodiments, the daily dose of metoclopramide is administered as 3-8 intranasal aliquots. In some embodiments, the daily dose of metoclopramide is administered as 3-8 intranasal aliquots of about 5 mg to 25 mg (e.g., 10 mg to 20 mg) of metoclopramide base per aliquot. In some embodiments, the daily dose of metoclopramide is administered as 3-8 intranasal aliquots of about 10 mg of metoclopramide base per aliquot. In some embodiments, each intranasal aliquot has a volume of about 25 μL to 150 μL. In some embodiments, each intranasal aliquot has a volume of about 50 μL. In some embodiments, the daily dose of metoclopramide is administered as 3-8 aliquots of about 14 mg metoclopramide base per aliquot. In some embodiments, each aliquot has a volume of approximately 25 μL to 150 μL. In some embodiments, each aliquot has a volume of approximately 70 μL. In some embodiments, the daily dose of metoclopramide is administered as 3 or 4 intranasal aliquots of about 20 mg of metoclopramide base per aliquot. In some particular embodiments, the intranasal aliquots are roughly equal. In some embodiments, each intranasal aliquot has a volume of about 50 μL to 150 μL. In some embodiments, the treatment of severe gastroparesis, such as severe female gastroparesis, includes treatment of severe diabetic gastroparesis, such as severe female diabetic gastroparesis. Some embodiments provide for use of a composition described herein for the preparation of a medicament for the treatment of severe gastroparesis, such as severe female gastroparesis, in particular female diabetic gastroparesis.

Some embodiments provide for a method of increasing the percentage of patients positively responding to metoclopramide administration in a gastroparesis patient population comprising: a. selecting from the total gastroparesis patient population, a treatment group consisting of patients having moderate to severe gastroparesis; and intranasally administering to patients in the treatment group; b. intranasally administering only to patients in the treatment group, a dose of 5 mg to 20 mg of intranasal metoclopramide, or a pharmaceutically acceptable salt thereof, 1 to 4 times per day, for a period of 1 to 12 weeks. Some embodiments provide for a method, further comprising: administering to patients having gastroparesis, who are not in the treatment group, a standard of care. Some embodiments provide for a method, wherein the standard of care is selected from the group consisting of oral or intravenous metoclopramide, pro-motility medications, antiemetic medications, pain medications, tricyclic antidepressants, specific meal plans or foods to consume/avoid, controlling glucose levels, correcting thyroid deficiencies, electrical pacing, and surgery. Some embodiments provide for a method, wherein the dose is 10 mg or 14 mg. Some embodiments provide for a method, wherein the treatment group consists of female patients having moderate to severe gastroparesis. Some embodiments provide for a method, wherein the treatment group consists of diabetic female patients having moderate to severe gastroparesis. Some embodiments provide for a method, wherein the intranasal metoclopramide administration treats one or more symptoms selected from the group consisting of nausea, bloating, early satiety, vomiting, feeling full, loss of appetite, stomach fullness, stomach being visibly larger, and upper abdominal discomfort. Some embodiments provide for a method of treating symptoms associated with gastroparesis, comprising: a. selecting human patients diagnosed with gastroparesis; b. selecting from the human patients diagnosed with gastroparesis a treatment group consisting of moderate to severe gastroparesis; c. intranasally administering only to patients in the treatment group a dose of 5 mg to 20 mg of intranasal metoclopramide, or a pharmaceutically acceptable salt thereof, 1 to 4 times per day, for a period of 1 to 12 weeks; and d. administering to patients diagnosed with gastroparesis, who are not in the treatment group, a standard of care. Some embodiments provide for a method, wherein the standard of care is selected from the group consisting of oral or intravenous metoclopramide, pro-motility medications, antiemetic medications, pain medications, tricyclic antidepressants, specific meal plans or foods to consume/avoid, controlling glucose levels, correcting thyroid deficiencies, electrical pacing, and surgery. Some embodiments provide for a method, wherein the dose is 10 mg or 14 mg. Some embodiments provide for a method, wherein the treatment group consists of female patients having moderate to severe gastroparesis. Some embodiments provide for a method, wherein the treatment group consists of diabetic female patients having moderate to severe gastroparesis. Some embodiments provide for a method, wherein the intranasal metoclopramide administration treats one or more symptoms selected from the group consisting of nausea, bloating, early satiety, vomiting, feeling full, loss of appetite, stomach fullness, stomach being visibly larger, and upper abdominal discomfort. Additional embodiments, features and advantages will become apparent upon consideration of the following detailed description of the invention.

INCORPORATION BY REFERENCE

All publications and patent applications mentioned in this specification are herein incorporated by reference to the same extent as if each individual publication or patent application was specifically and individually indicated to be incorporated by reference. In particular, U.S. Pat. No. 8,334,281 (D'Onofrio et al.) and U.S. Pre-Grant Publication 2013/0217775 are incorporated herein by reference in their entirety.

DETAILED DESCRIPTION OF THE INVENTION

The inventors have discovered that a treatment regimen of intranasal administration metoclopramide demonstrated statistically significant efficacy, as compared to placebo, against moderate to severe gastroparesis. The same treatment regimen did not demonstrate statistically significant efficacy, compared to placebo, for mild gastroparesis. Thus, the inventors have found that nasal administration of metoclopramide is effective in the treatment of moderate to severe gastroparesis, but not in the treatment of mild gastroparesis.

Thus, some embodiments described herein relate to a method of treating moderate or severe gastroparesis, and in some cases moderate to severe female gastroparesis, comprising administering to a human gastroparesis patient having (diagnosed as having, or suspected of having) moderate to severe gastroparesis an effective amount of metoclopramide or a pharmaceutically acceptable salt thereof. In some embodiments, the administration of metoclopramide is oral, buccal, sublingual, intranasal, pulmonary, topical, transdermal, rectal or intravenous route. In some preferred embodiments the administration of metoclopramide is intranasal. In some embodiments, administration is to both male and female humans with severe, or moderate to severe, gastroparesis, such as diabetic gastroparesis. Some embodiments relate to the treatment of severe or moderate to severe female gastroparesis, such as severe or moderate to severe female diabetic gastroparesis.

Thus, some embodiments described herein relate to a method of treating at least one, preferably two or more, symptoms of severe or moderate to severe gastroparesis, especially severe or moderate to severe female gastroparesis, comprising administering to a human patient (e.g., a human female patient) having (diagnosed with, or because of symptoms suspected of having, gastroparesis) an effective amount of metoclopramide or a pharmaceutically acceptable salt thereof In some embodiments, the administration of metoclopramide is oral, buccal, sublingual, intranasal, pulmonary, topical, transdermal, rectal or intravenous route. In some preferred embodiments the administration of metoclopramide is intranasal. Some embodiments provided herein relate to a method of treating at least one, preferably two or more, symptoms of severe or moderate to severe gastroparesis (e.g., moderate to severe female gastroparesis) selected from the group consisting of: nausea (feeling sick to your stomach as if you were going to vomit or throw up); retching (heaving as if to vomit, but nothing comes up); vomiting; stomach fullness; not able to finish a normal-sized meal; feeling excessively full after meals; loss of appetite; bloating; stomach or belly visibly larger; and upper abdominal pain (above the navel); upper abdominal discomfort (above the navel). Some embodiments relate to a method of treating two, three, four, five, six, seven, eight, nine, ten or all eleven of the symptoms selected from the group consisting of: nausea (feeling sick to your stomach as if you were going to vomit or throw up); retching (heaving as if to vomit, but nothing comes up); vomiting; stomach fullness; not able to finish a normal-sized meal; feeling excessively full after meals; loss of appetite; bloating; stomach or belly visibly larger; upper abdominal pain (above the navel); and upper abdominal discomfort (above the navel). In some embodiments, the severe or moderate to severe gastroparesis is severe or moderate to severe diabetic gastroparesis. In some embodiments, the severe or moderate to severe gastroparesis is severe or moderate to severe female gastroparesis. In some embodiments, the severe or moderate to severe gastroparesis is severe or moderate to severe female diabetic gastroparesis.

As used herein, the term "female gastroparesis" refers to gastroparesis experienced by human females in a treatment group consisting of females only, and excluding all males. Thus, "female gastroparesis" is identified by selecting from a group of gastroparesis patients only females, thereby forming a treatment group consisting of only female humans, and excluding all males, in which the female humans have been diagnosed with, or because of their symptoms are suspected of having, gastroparesis.

Treatment of gastroparesis, refers herein to relieving or ameliorating one or more symptoms of gastroparesis in members of a treatment group. In some embodiments, the treatment group consists only of female patients, and excludes all males. In some embodiments the treatment group includes both males and females. In some embodiments, the treatment group consists only of patients having severe or moderate to severe gastroparesis. In some embodiments the treatment group consists of patients having severe gastroparesis. In some embodiments the treatment group consists of patients having moderate to severe gastroparesis. In some embodiments, the treatment group consists of diabetic patients having severe or moderate to severe gastroparesis. In some embodiments, the group consists of female patients having severe or moderate to severe gastroparesis. In some embodiments the treatment group consists of female diabetic patients having severe or moderate to severe gastroparesis. In some embodiments, those one or more symptoms include upper abdominal pain, nausea, vomiting, or a combination of two or three thereof. In some embodiments the treatment group consisting of females only is obtained by selecting from human gastroparesis patients a group of patients consisting only of female humans and excluding all males. Treatment of "female gastroparesis" means treating female patients and not treating any males.

As used herein "metoclopramide" refers to metoclopramide in a solution formulation, including a salt of metoclopramide. In quantitating the mass of metoclopramide herein, unless otherwise specified, all masses of metoclopramide refer to the mass of the free base, which has a molecular weight of 299.80. One method of manufacturing metoclopramide is described in U.S. Pat. No. 3,177,252, which is incorporated herein by reference in its entirety. Thus, unless otherwise specified herein, the term "metoclopramide" includes the free base of metoclopramide (4-amino-5-chloro-N-[2-(diethylamino)ethyl]-2-methoxybenzamide) and pharmaceutically acceptable salts of metoclopramide free base. Where the "free base" or a specific salt of metoclopramide is intended, it is so specified. A particularly preferred form of metoclopramide is metoclopramide hydrochloride.

An "effective amount" of metoclopramide (or a pharmaceutically acceptable salt thereof) is an amount of metoclopramide that is effective to provide statistically significant relief from gastroparesis or one or more symptoms of gastroparesis in a cohort of humans, e.g., a cohort of human females (i.e., a cohort excluding all males). An "effective amount" is determined in comparison to administration of placebo. In some embodiments, efficacy is judged with reference to the Gastroparesis Cardinal Symptom Index-Daily Diary (GCSI-DD) and in some embodiments, efficacy is judged with reference to the modified GCSI-DD (mGCSI-DD), which is described in more detail herein. An additional symptom measurement instrument is the Gastroparesis Symptom Assessment (GSA) may be used to measure efficacy. Although not specifically measured in the referenced study, the GSA is derived from, and has similar statistical outcomes to the mGCSI-DD. See Example 1.

As provided herein, an effective amount of metoclopramide for the treatment moderate to severe gastroparesis, such as moderate to severe female gastroparesis, e.g., moderate to severe female diabetic gastroparesis, is ineffective to treat the symptoms associated with male gastroparesis, and thus males are excluded from the group of patients treated with metoclopramide. In some embodiments, the metoclopramide is administered to patients at a daily dose of approximately 20 mg to 60 mg of metoclopramide base per day. In some embodiments, the daily dose of metoclopramide is administered as 1 to 6 intranasal aliquots (e.g., sprays). In some embodiments, the daily dose of metoclopramide is administered as 4 intranasal aliquots. In some embodiments, the daily dose of metoclopramide is administered as 4 intranasal aliquots of about 5 mg to 15 mg of metoclopramide base per aliquot. In some embodiments, the daily dose of metoclopramide is administered as 4 intranasal aliquots of about 10 mg of metoclopramide base per aliquot. In some particular embodiments, the intranasal aliquots are roughly equal. In some embodiments, each intranasal aliquot has a volume of about 25 µL to 150 µL. In some embodiments, each intranasal aliquot has a volume of about 50 µL. In some embodiments, the daily dose of metoclopramide is administered as 4 aliquots of about 14 mg metoclopramide base per aliquot. In some embodiments, each aliquot has a volume of approximately 25 µL to 150 µL. In some embodiments, each aliquot has a volume of approximately 70 µL.

In some embodiments, the invention is directed toward administration of intranasal metoclopramide for the treatment of moderate to severe gastroparesis, e.g., moderate to severe female gastroparesis. Suitable formulations for such administration are taught in U.S. Pat. No. 8,334,281, which is incorporated herein in its entirety. Suitable methods for such administration are disclosed in U.S. Pre-Grant Publication 2013/0217775, which is incorporated herein by reference in its entirety.

In some embodiments described herein there is provided a nasal metoclopramide formulation and its use in the treatment of moderate to severe gastroparesis, e.g., moderate to severe female gastroparesis, comprising metoclopramide (or a pharmaceutically-acceptable salt thereof), citrate buffer and benzalkonium chloride having a pH of at least about 5. In some embodiments, the nasal metoclopramide formulation is one described in U.S. Pat. No. 8,334,281, which is incorporated herein in its entirety.

Some embodiments described herein provide a manufacture comprising a metoclopramide pharmaceutical composition, e.g., as described in U.S. Pat. No. 8,334,281, which is incorporated herein in its entirety. In some embodiments, the means for nasal administration comprises a reservoir that contains the composition, a pump in fluid communication with the composition in the reservoir and a nozzle in fluid communication with the pump, wherein activation of the pump withdraws a predetermined amount of said composition from the reservoir and causes said predetermined amount of said composition to be expelled from said nozzle. In some embodiments, the predetermined amount of composition is about 10 µL to about 200 µL, about 10 µL to about 150 µL, about 50 µL to about 150 µL, about 50 µL, about 55 µL, about 60 µL, about 75 µL, about 70 µL, about 75 µL, about 80 µL, about 85 µL, about 90 µL, about 95 µL, about 100 µL, about 110 µL, about 120 µL, about 125 µL, about 150 µL, about 175 µL or about 200 µL per activation ("spray" or "aliquot"). In order to combat the deleterious effects of light on metoclopramide, the manufacture may conveniently include a container, especially an opaque container, i.e. a container that is at least partially or completely impervious to light. In some embodiments, a suitable opaque container will be brown or amber, especially brown or amber glass. In other embodiments, the opaque container will be an opaque polymer container, such as is commonly used in the pharmaceutical arts.

As used herein, the indefinite articles "a" and "an" mean "at least one" unless otherwise stated. Likewise, the definite article "the", unless otherwise indicated, means "at least the" where the context permits or demands it to be open-ended.

As used herein, a "nasal administration device" is a device capable of administering a dose of a composition comprising metoclopramide into the nose of a patient. In some embodiments, the nasal administration device is an atomizer, comprising a reservoir adapted to contain the metoclopramide solution and a pump adapted to draw a predetermined amount of the metoclopramide solution from the reservoir dispense the predetermined amount of metoclopramide solution through an atomizing nozzle and into at least one nostril of a patient. Suitable nasal administration devices are commercially available.

As used herein, the term "spray" indicates an atomized volume of liquid expelled from a nozzle of a nasal administration device upon a single activation of the nasal administration device. In general, each spray is administered into a single nostril of a patient. As such, a "spray", as used herein, is a type of "aliquot", the latter being a generic term referring to an amount of liquid sprayed, instilled or otherwise introduced into a nostril of a subject, such as a patient.

As used herein, "metoclopramide" means metoclopramide (4-amino-5-chloro-N-(2-(diethylamino)ethyl)-2-methoxybenzamide) or a pharmaceutically acceptable salt thereof, such as the hydrochloride salt. Where reference is made to a particular mass of metoclopramide, the recited mass is that of the free base of metoclopramide, unless otherwise specified.

As used herein, "oral" means a dosage form taken by mouth, such as a tablet, powder, soft gel capsule, hard gel capsule, orally dissolving tablet or thin film, liquid, etc.

Other terms used herein have their art-recognized meanings, unless otherwise defined or described.

Gastroparesis and Symptoms of Gastroparesis

Described herein are methods for treating gastroparesis and symptoms of gastroparesis. Gastroparesis can be described as a disorder that slows or stops the movement of food from the stomach to the small intestine. A subject may be suspected of having gastroparesis if the subject exhibits or has exhibited a symptom of gastroparesis. Some symptoms of gastroparesis are selected from the group consisting of: nausea (feeling sick to your stomach as if you were going to vomit or throw up); retching (heaving as if to vomit, but nothing comes up); vomiting; stomach fullness; not able to finish a normal-sized meal; feeling excessively full after meals; loss of appetite; bloating; stomach or belly visibly larger; and upper abdominal pain (above the navel); upper abdominal discomfort (above the navel). Some embodiments relate to a method of treating two, three, four, five, six, seven, eight, nine, ten, or eleven of the symptoms selected from the group consisting of: nausea (feeling sick to your stomach as if you were going to vomit or throw up); retching (heaving as if to vomit, but nothing comes up); vomiting; stomach fullness; not able to finish a normal-sized meal; feeling excessively full after meals; loss of appetite; bloating; stomach or belly visibly larger; upper abdominal pain (above the navel); and upper abdominal discomfort (above the navel). In some embodiments, the gastroparesis is diabetic gastroparesis.

Formulation of Nasal Compositions of Metoclopramide (Use for Production of a Medicament)

Nasal compositions of metoclopramide may be manufactured for administration as a medicament for administration to a patient for one of the indications described herein. In some embodiments, the nasal metoclopramide formulation is one described in U.S. Pat. No. 8,334,281, which is incorporated herein in its entirety. Briefly, metoclopramide, buffer, benzalkonium chloride and optionally other ingredients (such as sodium chloride or other osmolarity-regulating agent, sorbitol or other sweetener, flavoring agent, etc.) may be made up to some volume less than the target final volume of the solution. The ingredients may then be mixed until all the ingredients are dissolved. The pH then may be adjusted, if necessary, by addition of a suitable acid or base, such as HCl, NaOH, or the complementary acid or base of the buffer. Once the desired pH has been obtained, the solution may then be brought up to full volume with water. The resulting solution may then be packaged in a suitable container for shipping and distribution. In some embodiments, the suitable container includes a nasal pump as described in more detail below. In other embodiments, the suitable container may be a vial, such as an amber glass vial, which may be a glass ampule, a glass bottle topped with an inert rubber septum and crimp cap top, or other suitable pharmaceutical vial.

Manufacture of Nasal Formulations

Some embodiments described herein provide, as a manufacture, a combination of a stable, clear and/or colorless solution of metoclopramide and a means for intranasal administration of the metoclopramide solution. In some embodiments, the manufacture comprises one of the metoclopramide solutions described herein and an intranasal delivery device comprising a reservoir, in which the metoclopramide solution is contained, a pump in fluid communication with the reservoir and a nozzle in fluid communication with the pump. In use, the pump is actuated, drawing an amount of the metoclopramide solution from the reservoir and expelling the solution out of the nozzle as an aerosolized spray. Suitable nasal administration devices are commercially available. Among the suppliers of nasal administration devices that may be combined with a stable, substantially clear and/or substantially colorless metoclopramide solution according to the present invention, there may be mentioned Aptar (Valois of America, Congers, New York, and Pfeiffer of America, Princeton, N.J.) In some embodiments, the intranasal delivery device is partially or completely opaque, in order to protect the contents of the device from exposure to ambient light.

Methods of Treatment with Nasally Administered Metoclopramide

The nasal metoclopramide formulations described herein may be employed in methods for the treatment of moderate to severe gastroparesis. The nasal metoclopramide formulations described herein may be employed in methods for the treatment of severe gastroparesis In some embodiments provided herein, relief of symptoms associated with moderate or severe gastroparesis, or moderate to severe gastroparesis, is treated by intranasal instillation of a pharmaceutically effective amount of an intranasal metoclopramide solution. In some embodiments, nasal metoclopramide is administered to female humans who have been diagnosed with gastroparesis. In some embodiments, an effective dose of nasal metoclopramide is administered to a human patient for about 1 to about 12 weeks, about 1 to 8 weeks, about 5 weeks to about 12 weeks, about 5 to about 8 weeks, or about 1, 2, 3, 4, 5, 6, 7, 8, 9, 10, 11, 12 or more weeks. In some embodiments the human patient is a member of a treatment group consisting of female humans, and excluding all males. In some embodiments the human has moderate to severe gastroparesis. In some embodiments, the human has severe gastroparesis.

In some embodiments, the effective daily dose of metoclopramide is about 20 mg/day to about 100 mg/day, which may be administered in 1 to 8, 1 to 6, 1 to 4 or 1 to 3 aliquots (e.g., "sprays"). In some embodiments, the daily dose of metoclopramide is about 40 mg/day to about 80 mg/day. In some embodiments in which the patient is renally impaired or coadministered with a drug known to alter metabolism or clearance of metoclopramide, the dose may be decreased by 25-75%, e.g., to a daily dose of 20 mg, which may be administered in e.g., 4 aliquots of 5 mg each or 2 aliquots of 10 mg each. In some embodiments, the daily dose administered to women is effective in female gastroparesis but not male gastroparesis. In some embodiments, the daily dose of nasal metoclopramide is about 30 mg/day to about 80 mg/day, administered in 1, 2, 3, 4, 5, 6, 7 or 8 aliquots. In some embodiments, the daily dose is 20, 22, 24, 25, 26, 28, 30, 32, 34, 35, 36, 38, 40, 42, 44, 45, 46, 48, 50, 52, 54, 55, 56, 58, 60, 62, 64, 66, 68, 70, 72, 74, 76, 78 or 80 mg/day administered in 1, 2, 3, 4, 5 or 6 aliquots. In some embodiments, the aliquots are substantially equivalent in volume. In some embodiments, the volumes of the aliquots (e.g., "sprays") are 25 µL to 150 µL, e.g., 25 µL to 100 µL, 30 µL to 80 µL, 40 µL to 75 µL. In some embodiments, the volumes of the aliquots are 25-60 µL, 30-70 µL, 40-60 µL, 50-90 µL or 60-80 µL. In some embodiments, the volumes of the aliquots are 20 µL, 22 µL, 24 µL, 25 µL, 26 µL, 28 µL, 30 µL, 32 µL, 34 µL, 35 µL, 36 µL, 38 µL, 40 µL, 42, µL, 44 µL, 45 µL, 46 µL, 48 µL, 50 µL, 55 µL, 54 µL, 55 µL, 56 µL, 58 µL, 60 µL, 62 µL, 64 µL, 65 µL, 66 µL, 68 µL, 70 µL, 72 µL, 74 µL, 75 µL, 76 µL, 78 µL, 80 µL, 82 µL, 84 µL, 85 µL, 86 µL, 88 µL, 90 µL, 92 µL, 94 µL, 95 µL, 96 µL, 98 µL or 100 µL. In some embodiments, the total effective daily dose is 40 mg/day of metoclopramide base or 56 mg/day of metoclopramide base administered in four aliquots (4×50 µL or 4×70 µL) throughout the day. In some embodiments, the total effective daily dose is 80 mg/day of metoclopramide base administered in 8 aliquots (one in each nostril, four times throughout the course of the day.

In some embodiments, the method comprises treatment of moderate to severe gastroparesis, such as moderate to severe female gastroparesis, of varying etiology, including moderate to severe gastroparesis, such as moderate to severe female gastroparesis, arising out, associated with or caused by diabetes (including type 1 and type 2), postviral syndromes, anorexia nervosa, surgery on the stomach or vagus nerve, medications, such as anticholinergic and narcotic medications, which tend to suppress intestinal and gastroesophageal contractions, gastroesophageal reflux disease, smooth muscle disorders (e.g., amyloidosis and scleroderma), nervous system diseases (including abdominal migraine and Parkinson's disease), and/or metabolic disorders (including hypothyroidism). In some such embodiments, the gastroparesis is severe gastroparesis.

In some embodiments, the gastroparesis is of diabetic origin, including type 1 and type 2 diabetes, and treatment comprises intranasally administering a nasal composition of metoclopramide as described herein in a nasal spray dosage form for about 1 to about 8 weeks, for about 2 weeks to about 8 weeks or for 1, 2, 3, 4, 5, 6, 7, 8 or more weeks.

Administration may be prescribed 30 minutes before meals, assuming 3 meals per day, and before bedtime. In some embodiments, doses are administered before breakfast and dinner. In some embodiments, each dose is administered as a single intranasal aliquot (e.g., spray); in some embodiments, each dose is administered as 2 aliquots (e.g., one spray per nostril).

In some embodiments, a pharmaceutical composition administered for the treatment of moderate to severe gastroparesis, such as moderate to severe female gastroparesis, as described herein consists of: metoclopramide (e.g., as metoclopramide HCl), citric acid (e.g., as the monohydrate), sodium citrate (e.g., as the dihydrate), benzalkonium chloride (e.g., as a 50% solution, N.F.), sorbitol (e.g., as a solution, such as a 70% solution USP), edetate disodium, sodium chloride and purified water. In some embodiments, a pharmaceutical composition administered for the treatment of female gastroparesis consists of: metoclopramide (e.g., as metoclopramide HCl), citric acid (e.g., as the monohydrate), sodium citrate (e.g., as the dihydrate), benzalkonium chloride (e.g., as a 50% solution, N.F.), edetate disodium, sodium chloride and purified water. In some embodiments, a pharmaceutical composition administered for the treatment of female gastroparesis consists of: metoclopramide (e.g., as metoclopramide HCl), citric acid (e.g., as the monohydrate), sodium citrate (e.g., as the dihydrate), benzalkonium chloride (e.g., as a 50% solution, N.F.), sodium chloride and purified water. In some such embodiments, the gastroparesis is severe gastroparesis, such as severe female gastroparesis.

The nasal metoclopramide compositions described herein may be administered a female patient as 1 spray in a single nostril, four times a day (1 spray QID for about 1, 2, 3, 4, 5, 6, 7, or 8 weeks), or 1 spray per nostril in both nostrils four times a day (2 sprays QID for about 1, 2, 3, 4, 5, 6, 7, or 8 weeks).

In some embodiments, nasal metoclopramide is administered in the absence of other gastroparesis medications. In some embodiments, additional medication may be administered if necessary. In some embodiments, the methods of treatment provided herein can also include co-administration of one or more additional therapeutic agents along with the metoclopramide nasal formulations described herein. The additional therapeutic agents administered concurrently with metoclopramide or at separate time intervals. In some embodiments, one or more other drugs may be incorporated into the metoclopramide nasal formulation. Additional therapeutic agents may include pain relievers, insulin and other drugs useful in the management of diabetes, steroids, especially steroids that prevent nasal irritation, and antidepressants.

Various techniques may be used to assess the severity of the gastroparesis and gastric emptying, and these will be well-known to those of skill in the art. Such techniques include questioning the patient regarding symptoms of gastroparesis by a Patient Reported Outcome (PRO) symptom measurement instrument. Techniques like octanoic breath test, wireless capsule endoscopy, radioscintigraphy, ultrasonography, and x-rays employing radiopaque markers such as barium, may be employed.

In some embodiments, a clinician will prescribe a lower dosage of metoclopramide because of an underlying medical condition or other clinical consideration. For example, in the case of renal impairment, the clinician will prescribe a dose that is appropriate for the degree of renal impairment or other rationale for slower metabolism or clearance of the metoclopramide, e.g., a dose that is 25% to 75% lower, in some embodiments 50% lower, than the dose prescribed for a patient without renal impairment. In some such embodiments, the daily dose will be 20 mg administered as two intranasal doses, e.g., one dose before breakfast and one before dinner. In some embodiments, each dose is administered as a single intranasal aliquot (e.g., spray). In some embodiments, each dose is administered as two intranasal aliquots (e.g., 2 sprays, one in each nostril).

The aforementioned dosages for the treatment and control of gastroparesis may be administered before meals and/or before bedtime. In some embodiments, each dose is administered as a single intranasal aliquot (e.g., 1 spray in one nostril); in some embodiments, the dose may be split into 2 or more intranasal aliquots (e.g., 2 sprays, one in each nostril).

Manufacture of Other Formulations

Some embodiments of the invention comprise administration of metoclopramide by oral, buccal, sublingual, pulmonary, topical, transdermal, rectal, or intravenous.

Metoclopramide may be orally administered. Suitable oral dosage forms include swallowed tablets, capsules, powders, and liquids. Suitable oral dosage forms also include orally disintegrating tablets, and soft gel capsules that release liquid in the mouth. Metoclopramide is available as an oral liquid and may be obtained from a number of commercial sources, such as Wockhardt under the name Metoclopramide Hydrochloride, as described in Abbreviated New Drug Application ANDA074703. Metoclopramide is also commercially available as an orally disintegrating tablet as Metozolv® ODT from Salix Pharmaceuticals, Inc., as described in New Drug Application NDA022246, and U.S. Pat. No. 6,413,549, which is incorporated herein by reference in its entirety. Metoclopramide is also commercially available as an oral (swallowed) tablet as Reglan® from ANI Pharmaceuticals, Inc., as described in New Drug Application NDA017854.

Metoclopramide may be administered buccally or sublingually. Suitable buccal forms include tablets, patches, and films that are applied to the buccal surface and are absorbed transmucosally. Buccal tablets are described in, inter alia, U.S. Pat. Nos. 7,651,698; 7,122,198; 6,916,485; 5,888,534; and 5,624,677. Buccal patches are described in, inter alia, U.S. Pat. No. 6,197,331. Sublingual forms include tablets and films, such as those described in U.S. Pat. Nos. 6,974,590; 6,572,891; 6,200,604; 5,888,534; and 5,624,677. Each of the foregoing patents is incorporated herein by reference in its entirety.

Metoclopramide may be administered by pulmonary inhalation. Metoclopramide may be administered as a dry powder, as a metered dose from a metered dose inhaler, or as a nebulized form from a nebulizer.

Metoclopramide may also be administered by topical or transdermal means. For transdermal administration, metoclopramide can be formulated into ointments, salves, gels, or creams as generally known in the art.

Metoclopramide may also be administered by intravenous administration. Intravenous metoclopramide is approved by the United States Food and Drug administration, and is available from Baxter Healthcare Corp. under the brand name REGLAN®. The intravenous solution is described in New Drug Application NDA017862.

Standard of Care

Some embodiments comprise treating patients with mild gastroparesis with the standard of care. In some embodiments, the standard of care is the course of action recommended by a treating physician. Thus, the standard of care may vary with an individual patient's prior treatment for gastroparesis. Additionally, the standard of care can include experimental treatments. In some embodiments, the standard of care includes administering metoclopramide. In some embodiments, the metoclopramide may be orally administered, including, but not limited to, swallowed tablets, capsules, powders, and liquids. In some embodiments, the standard of care includes administering pro-motility medications. In some embodiments, the pro-motility medications can include, but are not limited to, dopamine receptor antagonists, including, domperidone, itopride, levosulpiride. In some embodiments, the pro-motility medications can include, but are not limited to, motilin receptor agonists, including, erythromycin, or other macrolide antibiotics such as azithromycin or clarithromycin, and mitemcinal. In some embodiments, the pro-motility medications can include, but are not limited to, 5-HT4 receptor antagonists, including cisapride, mosapride, renzapride, or tegaserod. In some embodiments, the pro-motility medications can include other agents, including, but not limited to acotiamide hydrochloride, neostigmine, ghrelin, cholecystokinin receptor antagonists, opioid receptor antagonists, alpha-adrenoceptor agonists, $GABA_B$ receptor agonists. In some embodiments, the standard of care includes administering antiemetics. In some embodiments, the antiemetics can include phenothiazines. In some embodiments, the antiemetics can include 5-HT3 antagonists, including, but not limited to, ondansetron, granisetron, dolasetron, and tropisetron. In some embodiments, the antiemetics can include antihistamines, including, but not limited to, H-1 receptor antagonists. In some embodiments, the antiemetics can include NK-1 antagonists, including, but not limited to aprepitant. In some embodiments, the antiemetics can include cannabinoids, including, but not limited to delta-9-tetrhydrocannabinol and nabilone. In some embodiments, the standard of care includes psychopharmacology. In some embodiments, the psychopharmacology can include tricyclic antidepressants, including but not limited to amitriptyline, nortriptyline, and desipramine. In some embodiments, the psychopharmacology can include mirtazapine. In some embodiments, the psychopharmacology can include antimuscarinic agents, including, but not limited to, transdermal scopolamine. In some embodiments, the psychopharmacology can include benzodiazepines, including, but not limited to lorazepam. In some embodiments, the psychopharmacology can include prostaglandins. In some embodiments, the psychopharmacology is a dopamine 2 receptor antagonist, including, but not limited to droperidol. In some embodiments, the standard of care includes pain medications. In some embodiments, the pain medication is a NSAID (non-steroidal anti-inflammatory drug), including, but not limited to ketorolac and indomethacin. In some embodiments, the pain medication is an opiate analgesic, including, but not limited to tramadol. In some embodiments, the pain medication is a 5HT-1A receptor agonist, including, but not limited to, buspirone. In some embodiments, the pain medication is an SSRI (selective serotonin reuptake inhibitor), including, but not limited to paroxetine and citalopram. In some embodiments, the pain medication is a serotonin-norepinephrine reuptake inhibitor, including, but not limited to duloxetine and venlafaxine. In some embodiments, the pain medication is an antiepileptic, including, but not limited to gabapentin and pregabalin. In some embodiments, the pain medication is a kappa-opioid agonist, including, but not limited to asimadoline. In some embodiments, the pain medication is a transient receptor vanillioid 4 or transient receptor vanillioid 1 receptor. In some embodiments, the standard of care is a meal plan. In some embodiments, the standard of care is diet instructions to consume or not consume certain foods. In some embodiments, the meal plan or diet instruction is to consume soft foods. In some embodiments, the meal plan or diet instruction is to consume smaller, more frequent meals. In some embodiments, the meal plan or diet instruction is to consume less fatty foods. In some embodiments, the meal plan or diet instruction is to avoid fiber and foods high in fiber. In some embodiments, the standard of care is to control, manage, or treat the underlying cause of the gastroparesis. In some embodiments, the standard of care is to lower and/or control glucose levels in a diabetic patient. In some embodiments, the standard of care is to treat thyroid deficiencies. In some embodiments, the standard of care is electrical pacing. In some embodiments, the standard of care is surgery.

Severity of Gastroparesis

In some embodiments, gastroparesis patients are treated according to the severity of the gastroparesis. In some embodiments, treatment of gastroparesis includes treatment of mild gastroparesis, as defined by the mGCSI-DD or GSA. In some embodiments, the treatment of gastroparesis includes treatment of moderate gastroparesis, as defined by the mGCSI-DD or GSA. In some embodiments, the treatment of gastroparesis includes treatment of severe gastroparesis, as defined by the mGCSI-DD or GSA. In some embodiments, the treatment of gastroparesis includes treatment of moderate or severe gastroparesis, as defined by the mGCSI-DD or GSA. In some embodiments, the treatment of gastroparesis includes treatment of moderate or severe gastroparesis, as defined by another self-reported outcome measurement tool. In some embodiments, the treatment of gastroparesis includes treatment of moderate or severe gastroparesis by a physician reported outcome measurement tool or by physician clinical assessment.

Gastroparesis Cardinal Symptom Index-Daily Diary (GCSI-DD)

In some embodiments, the severity of the gastroparesis is assessed by the Gastroparesis Cardinal Symptom Index-Daily Diary (GCSI-DD). The GCSI-DD, and the modified GCSI-DD (mGCSI-DD) are self-reported assessment of severity of gastroparesis symptoms. For each symptom, patients are instructed to choose the number (0-5) that best describes the severity of the symptom during the previous 24 hours. 0=none; 1=very mild; 2=mild; 3=moderate; 4=severe; 5=very severe. In general, patients with a mean GCSI-DD score of <2.0 are considered to have very mild to mild gastroparesis symptoms. Similarly, patients with a mean GCSI-DD score of approximately 3 are considered to have moderate gastroparesis symptoms. Additionally, patients with a mean GCSI-DD score of approximately 4 or greater are considered to have severe to very severe gastroparesis symptoms.

Other Reporting/Measuring Tools

In some embodiments, the severity of the gastroparesis is assessed by the Gastroparesis Symptom Assessment (GSA). The GSA is another patient reported outcome tool. The GSA is derived from, and has similar statistical outcomes to the mGCSI-DD. In some embodiments, the severity of the gastroparesis is assessed by the patient assessment of upper gastrointestinal disorders-symptom severity index (PAGI-SYM). The PAGI-SYM is another patient reported outcome tool. The PAGI-SYM has six subscales: heartburn/regurgitation, fullness/early satiety, nausea/vomiting, bloating, upper abdominal pain, and lower abdominal pain. In other embodiments, the severity of the gastroparesis can be assessed by other patient reported outcome tools or by physician reported outcome tools. The current recommendation by the Food and Drug Administration (FDA) in the development and selection of outcome tracking tools is that the outcome tool should include daily recordation of signs and symptoms to minimize inaccurate responses resulting from problems with patient recall. Additionally, outcome tools should rate all signs and symptoms (except vomiting) by severity, and that vomiting should be measured by frequency rather than severity. See *Gastroparesis: Clinical Evaluation of Drugs for Treatment: Guidance for Industry*, FDA, U.S. HHS, July 2015.

EXAMPLES

Example 1

Multicenter Study to Evaluate the Efficacy and Safety of Metoclopramide Nasal Spray in Women With Diabetic Gastroparesis A multicenter, randomized, double-blind, placebo-controlled clinical study of intranasal metoclopramide ("IN MCP") in female diabetic gastroparesis patients was carried out. The study explored the use of IN MCP for the relief of symptoms associated with acute and recurrent diabetic gastroparesis in adult women. As summarized below, study data demonstrated that patients with moderate to severe symptoms responded statistically significantly better to IN MCP than those treated with placebo at multiple time points (Table 1). There were also clinically and statistically significant improvements in nausea and abdominal pain, which are two of the more severe and debilitating symptoms of gastroparesis (Table 2).

The study was a U.S. multicenter, randomized, double-blind, placebo-controlled, parallel-group study of the efficacy and safety of IN MCP compared to placebo in adult female subjects with diabetic gastroparesis. Diabetic women with clinical symptoms attributed to diabetic gastroparesis, and documentation of delayed gastric emptying who met the protocol-specified entry criteria were randomized 1:1 in a parallel-group design to IN MCP (10 mg metoclopramide) or placebo administered as a single nasal spray four times daily; 30 minutes before meals and at bedtime for a total of four weeks. Eligible patients received a dose of IN MCP or placebo 30 minutes before meals and at bedtime daily.

A total of 205 female gastroparesis patients were enrolled. Of the total, nearly half had been identified as having moderate to severe gastroparesis. A treatment regimen consisting of intranasal administration of 10 mg of metoclopramide four times daily (q.i.d.) resulted in no statistically significant change from baseline in efficacy versus placebo for all enrolled patients across all severities of disease. However, a post-hoc analysis demonstrated that the treatment regimen resulted in statistically significant efficacy in patients who entered the study with moderate to severe gastroparesis.

Diabetic women with clinical symptoms attributed to diabetic gastroparesis and documentation of delayed gastric emptying who met the protocol-specified entry criteria were randomized to Metoclopramide Nasal Spray 10 mg or placebo administered as a single intranasal spray four (4) times daily; 30 minutes before meals and at bedtime for a total of four (4) weeks.

Inclusion criteria included prior diagnosis of Type 1 or Type 2 diabetes, and diagnosis of diabetic gastroparesis with delayed gastric emptying. Evaluation was carried out using patient reported outcomes at baseline and Week 4 of the study.

The patient segment with moderate to severe symptoms of gastroparesis, representing approximately 50% of total subjects, indicated a greater improvement in symptoms when treated with intranasal metoclopramide (IN MCP) versus those treated with placebo (Table 1). There were also clinically and statistically significant improvements in nausea and abdominal pain, which are two of the more severe and debilitating symptoms of gastroparesis, in this patient population.

TABLE 1

Phase 3 Estimated Mean Change from Baseline in Mean Daily GSA Total Scores: Study Populations with Baseline GSA >2.7 (BOCF)

|  | Time Period | Placebo 1 | IN MCP 10 mg[1] | p-value[2] |
|---|---|---|---|---|
|  |  | (N = 53) | (N = 52) |  |
| ITT Baseline >2.7 | Week 1 | −0.387 | −0.588 | 0.036 |
|  | Week 2 | −0.614 | −0.950 | 0.025 |
|  | Week 3 | −0.749 | −1.096 | 0.039 |
|  | Week 4 | −0.856 | −1.220 | 0.085* |
|  |  | (N = 40) | (N = 38) |  |
| Per Protocol Baseline >2.7 | Week 1 | −0.362 | −0.623 | 0.019 |
|  | Week 2 | −0.625 | −1.040 | 0.015 |
|  | Week 3 | −0.714 | −1.286 | 0.003 |
|  | Week 4 | −0.841 | −1.373 | 0.014 |

[1]LSMean from ANCOVA;
[2]p-value is obtained from an ANCOVA model with fixed effect for treatment group and the baseline value as a covariate. If the normality assumption was not met, the p-value was obtained from a rank ANCOVA test and denoted with an *.

Overall safety results from the study revealed no significant adverse effects. In particular, there were no central nervous system (CNS) effects observed with IN MCP delivered as a nasal spray that have been associated with oral and parenteral metoclopramide (Table 3). There have been no reports of tardive dyskinesia among the 1,311 exposed healthy volunteers and patients over the clinical development program.

TABLE 2

Mean Change from Baseline to Week 4 in Mean Daily Nausea and Upper Abdominal Pain Score in ITT Population with Moderate to Severe Symptoms

| Symptom | Time Period | Placebo 1 (N = 53) | IN MCP 10 mg[1] (N = 52) | p-value[2] |
|---|---|---|---|---|
| Nausea | Week 1 | −0.370 | −0.859 | 0.001 |
|  | Week 2 | −0.696 | −1.149 | 0.032* |
|  | Week 3 | −0.818 | −1.242 | 0.043 |
|  | Week 4 | −0.905 | −1.404 | 0.027 |
| Upper Abdominal Pain | Week 1 | −0.394 | −0.641 | 0.025 |
|  | Week 2 | −0.554 | −0.990 | 0.016 |
|  | Week 3 | −0.690 | −1.194 | 0.008 |
|  | Week 4 | −0.791 | −1.218 | 0.047 |

[1]LSMean from ANCOVA
[2]p-value is obtained from an ANCOVA model with fixed effect for treatment group and the baseline value as a covariate. If the normality assumption was not met, the p-value was obtained from a rank ANCOVA test and denoted with an *.

TABLE 3

Selected Treatment-Emergent Adverse Events Reported by More than 2 Subjects in Any Treatment Group

| Adverse Event | Placebo (N = 103) | IN MCP 10 mg (N = 102) |
|---|---|---|
| Headache | 7 (7%) | 5 (5%) |
| Nasal discomfort | 4 (4%) | 1 (1%) |
| Epistaxis | 2 (2%) | 1 (1%) |
| Fatigue | 1 (1%) | 2 (2%) |

One of the more significant outcomes from the analysis of the separated patient groups were results on the improvement in symptom scores when looking at moderate and severe patients, which consisted of a large portion of the overall population. In this group, those treated with IN MCP reported significantly better results than those who received placebo. Furthermore, nausea and abdominal pain, two of the more severe and common symptoms of gastroparesis, showed the most improvement from patients treated with the drug, which was also observed in the Phase 2B trial.

Patients suffering from moderate to severe flares of gastroparesis are often unable to find relief with oral metoclopramide and often require hospital stays. IN MCP has demonstrated a clear and positive safety profile with no reported drug-related adverse effects.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The disclosure herein is further clarified in reference to a partial list of numbered embodiments as follows: 1. A method of treating moderate to severe gastroparesis, comprising administering to human gastroparesis patients an amount of metoclopramide or a pharmaceutically acceptable salt thereof effective to treat moderate to severe gastroparesis. 2. The method of embodiment 1, wherein such administration is oral, buccal, sublingual, intranasal, pulmonary, topical, transdermal, rectal or intravenous. 3. The method of embodiment 1, wherein such administration is intranasal. 4. The method of one of embodiments 1-3, wherein the effective amount of metoclopramide is ineffective to treat mild gastroparesis. 5. The method of one of embodiments 1-4, wherein said human gastroparesis patients are members of a female gastroparesis treatment group consisting of female human patients only, and excluding all males, said method further comprising establishing said female gastroparesis treatment group consisting of female human patients only, and excluding all males, prior to administering the amount of metoclopramide or pharmaceutically acceptable salt thereof to said human gastroparesis patients who are members of said female gastroparesis treatment group consisting of female human patients only, and excluding all males. 6. The method of one of embodiments 1-5, wherein the metoclopramide is administered at a daily dose of approximately 40 mg to 80 mg of metoclopramide base per day. 7. The method of one of embodiments 1-6, wherein the daily dose of metoclopramide is administered as 1 to 8 intranasal aliquots. 8. The method of one of embodiments 1-7, wherein the daily dose of metoclopramide is administered as aliquots of 25 μL to 150 μL. 9. The method of embodiment 7, wherein the daily dose of metoclopramide is administered as 3-8 intranasal aliquots. 10. The method of one of embodiments 1-9, wherein the daily dose of metoclopramide is administered as 3-8 intranasal aliquots of about 5 mg to 25 mg of metoclopramide base per aliquot. 11. The method of one of embodiments 1-10, wherein the daily dose of metoclopramide is administered as 3-8 intranasal aliquots of about 10 mg of metoclopramide base per aliquot. 12. The method of embodiment 11, wherein each aliquot has a volume of about 25 μL to 150 μL. 13. The method of embodiment 11, wherein each aliquot has a volume of about 50 μL. 14. The method of one of embodiments 1-10, wherein the daily dose of metoclopramide is administered as 4 aliquots of about 14 mg metoclopramide base per aliquot. 15. The method of embodiment 14, wherein each aliquot has a volume of approximately 25 μL to 150 μL. 16. The method of embodiment 15, wherein each aliquot has a volume of approximately 70 μL. 17. The method of one of embodiments 1-16, wherein the female gastroparesis is female diabetic gastroparesis. 18. The method of one of embodiments 1-17, wherein the method improves quality of life of a subject afflicted with female gastroparesis. 19. The method of one of embodiments 1-18, wherein one or more symptoms of female gastroparesis are treated, and one or more symptoms that are treated are: a. upper abdominal pain associated with female gastroparesis; b. nausea associated with female gastroparesis; c. bloating associated with female gastroparesis; d. satiety associated with female gastroparesis; e. vomiting associated with female gastroparesis; f. retching associated with female gastroparesis; g. feeling full (inability to finish a meal) associated with female gastroparesis; h. loss of appetite associated with female gastroparesis; i. stomach fullness associated with female gastroparesis; j. stomach being visibly larger associated with female gastroparesis; and/or k. upper abdominal discomfort associated with female gastroparesis. 20. The method of embodiment 19, wherein such administration is oral, buccal, sublingual, intranasal, pulmonary, topical, transdermal, rectal or intravenous. 21. The method of one of embodiments 19 and 20, wherein such administration is intranasal. 22. The method of one of embodiments 19-21, wherein the effective amount of metoclopramide is ineffective to treat male gastroparesis. 23. The method of one of embodiments 19-22, wherein the metoclopramide is administered at a daily dose of approximately 20 mg to 100 mg of metoclopramide base per day. 24. The method of one of embodiments 19-23, wherein the metoclopramide is administered at a daily dose of approximately 40 mg to 80 mg of metoclopramide base per day. 25. The method of one of embodiments 19-24, wherein the daily dose of metoclopramide is administered as 1 to 8 intranasal aliquots. 26. The method of one of embodiments 19-25, wherein the daily dose of metoclopramide is administered as aliquots of 25 μL to 150 μL. 27. The method of one of embodiments 19-24, wherein the daily dose of metoclopramide is administered as 3-8 intranasal aliquots. 28. The method of one of embodiments 19-24, wherein the daily dose of metoclopramide is administered as 3-8 intranasal aliquots of about 5 mg to 25 mg of metoclopramide base per aliquot. 29. The method of one of embodiments 19-24, wherein the daily dose of metoclopramide is administered as 3-8 intranasal aliquots of about 10 mg of metoclopramide base per aliquot. 30. The method of one of embodiments 27-29, wherein each aliquot has a volume of about 25 μL to 150 μL. 31. The method of embodiment 30, wherein each aliquot has a volume of about 50 μL. 32. The method of embodiment 28, wherein the daily dose of metoclopramide is administered as 4 aliquots of about 14 mg metoclopramide base per aliquot. 33. The method of embodiment 28, wherein each aliquot has a volume of approximately 25 μL to 150 μL. 34. The method of embodiment 33, wherein each aliquot has a volume of approximately 70 μL. 35. The method of one of embodiments 19-34, wherein the female gastroparesis is female diabetic gastroparesis. 36. A method of treating moderate to severe gastroparesis in human patients, comprising: a. establishing a group consisting of human patients diagnosed with, or suspected of having gastroparesis, and excluding human patients diagnosed with, or suspected of having, mild gastroparesis to form a treatment group consisting of human patients diagnosed with, or suspected of having moderate to severe gastroparesis; b. administering to patients in said treatment group an amount of metoclopramide, or pharmaceutically acceptable salt thereof, effective to treat said moderate to severe gastroparesis; and c. not administering said metoclopramide, or pharmaceutically acceptable salt thereof, to said human patients diagnosed with, or suspected of having, mild gastroparesis. 37. The method of embodiment 36, wherein said metoclopramide, or pharmaceutically acceptable salt thereof, is administered intranasally. 38. The method of embodiment 35 or embodiment 36, wherein said treatment group consisting of human patients diagnosed with, or suspected of having gastroparesis, and excluding human patients diagnosed with, or suspected of having, mild gastroparesis, excludes all male patients. 39. A method of treating severe gastroparesis, comprising administering to human gastroparesis patients an amount of metoclopramide or a pharmaceutically acceptable salt thereof effective to treat moderate to severe gastroparesis. 40. The method of embodiment 39, wherein such administration is oral, buccal, sublingual, intranasal, pulmonary, topical, transdermal, rectal or intravenous. 41. The method of embodiment 39, wherein such administration is intranasal. 42. The method of one of embodiments 39-41, wherein the effective amount of metoclopramide is ineffective to treat mild or moderate gastroparesis. 43. The method of one of embodiments 39-42, wherein said human gastroparesis patients are members of a female gastroparesis treatment group, said method further comprising establishing said female gastroparesis treatment group consisting of female human patients only, and excluding all males, prior to administering the amount of metoclopramide or pharmaceutically acceptable salt thereof to said human gastroparesis patients who are members of said female gastroparesis treatment group. 44. The method of one of embodiments 39-43, wherein the metoclopramide is administered at a daily dose of approximately 40 mg to 80 mg of metoclopramide base per day. 45. The method of one of embodiments 39-44, wherein the daily dose of metoclopramide is administered as 1 to 8 intranasal aliquots. 46. The method of one of embodiments 39-45, wherein the daily dose of metoclopramide is administered as aliquots of 25 µL to 150 µL. 47. The method of one of embodiments 39-46, wherein the daily dose of metoclopramide is administered as 3-8 intranasal aliquots. 48. The method of one of embodiments 39-46, wherein the daily dose of metoclopramide is administered as 3-8 intranasal aliquots of about 5 mg to 25 mg of metoclopramide base per aliquot. 49. The method of one of embodiments 39-48, wherein the daily dose of metoclopramide is administered as 3-8 intranasal aliquots of about 10 mg of metoclopramide base per aliquot. 50. The method of embodiment 49, wherein each aliquot has a volume of about 25 µL to 150 µL. 51. The method of embodiment 49, wherein each aliquot has a volume of about 50 µL. 52. The method of one of embodiments 39-48, wherein the daily dose of metoclopramide is administered as 4 aliquots of about 14 mg metoclopramide base per aliquot. 53. The method of embodiment 52, wherein each aliquot has a volume of approximately 25 µL to 150 µL. 54. The method of embodiment 53, wherein each aliquot has a volume of approximately 70 µL. 55. The method of one of embodiments 39-54, wherein the female gastroparesis is female diabetic gastroparesis. 56. The method of one of embodiments 39-55, wherein the method improves quality of life of a subject afflicted with female gastroparesis. 57. The method of one of embodiments 39-56, wherein one or more symptoms of female gastroparesis that are treated are: a. upper abdominal pain associated with female gastroparesis; b. nausea associated with female gastroparesis; c. bloating associated with female gastroparesis; d. satiety associated with female gastroparesis; e. vomiting associated with female gastroparesis; f. retching associated with female gastroparesis; g. feeling full (inability to finish a meal) associated with female gastroparesis; h. loss of appetite associated with female gastroparesis; i. stomach fullness associated with female gastroparesis; j. stomach being visibly larger associated with female gastroparesis; and/or k. upper abdominal discomfort associated with female gastroparesis. 58. The method of embodiment 57, wherein such administration is oral, buccal, sublingual, intranasal, pulmonary, topical, transdermal, rectal or intravenous. 59. The method of embodiment 58, wherein such administration is intranasal. 60. The method of one of embodiments 57-59, wherein the effective amount of metoclopramide is ineffective to treat male gastroparesis. 61. The method of one of embodiments 57-60, wherein the metoclopramide is administered at a daily dose of approximately 20 mg to 100 mg of metoclopramide base per day. 62. The method of one of embodiments 57-61, wherein the metoclopramide is administered at a daily dose of approximately 40 mg to 80 mg of metoclopramide base per day. 63. The method of one of embodiments 57-62, wherein the daily dose of metoclopramide is administered as 1 to 8 intranasal aliquots. 64. The method of one of embodiments 57-63, wherein the daily dose of metoclopramide is administered as aliquots of 25 µL to 150 µL. 65. The method of one of embodiments 57-62, wherein the daily dose of metoclopramide is administered as 3-8 intranasal aliquots. 66. The method of one of embodiments 57-62, wherein the daily dose of metoclopramide is administered as 3-8 intranasal aliquots of about 5 mg to 25 mg of metoclopramide base per aliquot. 67. The method of one of embodiments 57-62, wherein the daily dose of metoclopramide is administered as 3-8 intranasal aliquots of about 10 mg of metoclopramide base per aliquot. 68. The method of embodiment 67, wherein each aliquot has a volume of about 25 µL to 150 µL. 69. The method of embodiment 68, wherein each aliquot has a volume of about 50 µL. 70. The method of one of embodiments 57-62, wherein the daily dose of metoclopramide is administered as 4 aliquots of about 14 mg metoclopramide base per aliquot. 71. The method of embodiment 70, wherein each aliquot has a volume of approximately 25 µL to 150 µL. 72. The method of embodiment 71, wherein each aliquot has a volume of approximately 70 µL. 73. The method of one of embodiments 57-72, wherein the female gastroparesis is female diabetic gastroparesis. 74. A method of treating severe gastroparesis in human patients, comprising: a. establishing a group consisting of human patients diagnosed with, or suspected of having, gastroparesis, and excluding human patients diagnosed with, or suspected of having, mild to moderate gastroparesis to form a treatment group consisting of human patients diagnosed with, or suspected of having, severe gastroparesis; b. administering to patients in said treatment group an amount of metoclopramide, or pharmaceutically acceptable salt thereof, effective to treat said moderate to severe gastroparesis; and c. not administering said metoclopramide, or pharmaceutically acceptable salt thereof, to said human patients diagnosed with, or suspected of having, mild gastroparesis. 75. The method of embodiment 74, wherein said metoclopramide, or pharmaceutically acceptable salt thereof, is administered intranasally. 76. The method of embodiment 74 or embodiment 75, wherein said treatment group consisting of human patients diagnosed with, or suspected of having, severe gastroparesis, and excluding human patients diagnosed with, or suspected of having, mild to moderate gastroparesis, excludes all male patients. 77. A method of treating upper abdominal pain, nausea, or both, in patients having moderate to severe gastroparesis, comprising administering to human gastroparesis patients an amount of metoclopramide or a pharmaceutically acceptable salt thereof effective to treat upper abdominal pain, nausea, or both in said patients having moderate to severe gastroparesis. 78. The method of embodiment 77, wherein such administration is oral, buccal, sublingual, intranasal, pulmonary, topical, transdermal, rectal or intravenous. 79. The method of embodiment 77, wherein such administration is intranasal. 80. The method of one of embodiments 77-79, wherein the effective amount of metoclopramide is ineffective to treat mild gastroparesis. 81. The method of one of embodiments 77-80, wherein said human gastroparesis patients are members of a female gastroparesis treatment group consisting of female human patients only, and excluding all males, said method further comprising establishing said female gastroparesis treatment group consisting of female human patients only, and excluding all males, prior to administering the amount of metoclopramide or pharmaceutically acceptable salt thereof to said human gastroparesis patients who are members of said female gastroparesis treatment group consisting of female human patients only, and excluding all males. 82. The method of one of embodiments 77-81, wherein the metoclopramide is administered at a daily dose of approximately 40 mg to 80 mg of metoclopramide base per day. 83. The method of one of embodiments 77-82, wherein the daily dose of metoclopramide is administered as 1 to 8 intranasal aliquots. 84. The method of one of embodiments 77-83, wherein the daily dose of metoclopramide is administered as aliquots of 25 µL to 150 µL. 85. The method of one of embodiments 77-84, wherein the daily dose of metoclopramide is administered as 3-8 intranasal aliquots. 86. The method of one of embodiments 77-84, wherein the daily dose of metoclopramide is administered as 3-8 intranasal aliquots of about 5 mg to 25 mg of metoclopramide base per aliquot. 87. The method of one of embodiments 77-84, wherein the daily dose of metoclopramide is administered as 3-8 intranasal aliquots of about 10 mg of metoclopramide base per aliquot. 88. The method of embodiment 87, wherein each aliquot has a volume of about 50 µL. 89. The method of one of embodiments 77-84, wherein the daily dose of metoclopramide is administered as 4 aliquots of about 14 mg metoclopramide base per aliquot. 90. The method of embodiment 89, wherein each aliquot has a volume of approximately 70 µL. 91. The method of one of embodiments 77-90, wherein the female gastroparesis is female diabetic gastroparesis. 92. The method of one of embodiments 77-91, wherein the method improves quality of life of a subject afflicted with female gastroparesis. 93. The method of one of embodiments 77-92, wherein two or more symptoms of female gastroparesis are treated, and two or more such symptoms are selected from the group consisting of: a. upper abdominal pain associated with female gastroparesis; b. nausea associated with female gastroparesis; c. bloating associated with female gastroparesis; d. satiety associated with female gastroparesis; e. vomiting associated with female gastroparesis; f retching associated with female gastroparesis; g. feeling full (inability to finish a meal) associated with female gastroparesis; h. loss of appetite associated with female gastroparesis; i. stomach fullness associated with female gastroparesis; j. stomach being visibly larger associated with female gastroparesis; and/or k. upper abdominal discomfort associated with female gastroparesis, wherein at least one of said symptoms is upper abdominal pain or nausea. 94. The method of embodiment 93, wherein such administration is oral, buccal, sublingual, intranasal, pulmonary, topical, transdermal, rectal or intravenous. 95. The method of embodiment 93, wherein such administration is intranasal. 96. The method of one of embodiments 93-95, wherein the effective amount of metoclopramide is ineffective to treat male gastroparesis. 97. The method of one of embodiments 93-96, wherein the metoclopramide is administered at a daily dose of approximately 20 mg to 100 mg of metoclopramide base per day. 98. The method of one of embodiments 93-97, wherein the metoclopramide is administered at a daily dose of approximately 40 mg to 80 mg of metoclopramide base per day. 99. The method of one of embodiments 93-98, wherein the daily dose of metoclopramide is administered as 1 to 8 intranasal aliquots. 100. The method of one of embodiments 93-99, wherein the daily dose of metoclopramide is administered as aliquots of 25 µL to 150 µL. 101. The method of one of embodiments 93-100, wherein the daily dose of metoclopramide is administered as 3-8 intranasal aliquots. 102. The method of one of embodiments 93-100, wherein the daily dose of metoclopramide is administered as 3-8 intranasal aliquots of about 5 mg to 25 mg of metoclopramide base per aliquot. 103. The method of one of embodiments 93-100, wherein the daily dose of metoclopramide is administered as 3-8 intranasal aliquots of about 10 mg of metoclopramide base per aliquot. 104. The method of embodiment 103, wherein each aliquot has a volume of about 50 µL. 105. The method of one of embodiments 93-100, wherein the daily dose of metoclopramide is administered as 4 aliquots of about 14 mg metoclopramide base per aliquot. 106. The method of embodiment 105, wherein each aliquot has a volume of approximately 70 µL. 107. The method of one of embodiments 93-106, wherein the female gastroparesis is female diabetic gastroparesis. 108. The method of one of embodiments 77-107, wherein upper abdominal pain and nausea are treated. 109. A method of treating upper abdominal pain, nausea, or both, in patients having moderate to severe gastroparesis in human patients, comprising: a. establishing a group consisting of human patients diagnosed with, or suspected of having gastroparesis, and excluding human patients diagnosed with, or suspected of having, mild gastroparesis to form a treatment group consisting of human patients diagnosed with, or suspected of having moderate to severe gastroparesis; b. administering to patients in said treatment group an amount of metoclopramide, or pharmaceutically acceptable salt thereof, effective to treat said moderate to severe gastroparesis; and c. not administering said metoclopramide, or pharmaceutically acceptable salt thereof, to said human patients diagnosed with, or suspected of having, mild gastroparesis. 110. The method of embodiment 109, wherein said metoclopramide, or pharmaceutically acceptable salt thereof, is administered intranasally. 111. The method of embodiment 109 or embodiment 110, wherein said treatment group consisting of human patients diagnosed with, or suspected of having gastroparesis, and excluding human patients diagnosed with, or suspected of having, mild gastroparesis, excludes all male patients. 112. The method of one of embodiments 109-111, wherein upper abdominal pain and nausea are treated. 114. A method of treating severe gastroparesis, comprising administering to human gastroparesis patients an amount of metoclopramide or a pharmaceutically acceptable salt thereof effective to treat moderate to severe gastroparesis. 115. The method of embodiment 114, wherein such administration is oral, buccal, sublingual, intranasal, pulmonary, topical, transdermal, rectal or intravenous. 116. The method of embodiment 114, wherein such administration is intranasal. 117. The method of one of embodiments 114-116, wherein the effective amount of metoclopramide is ineffective to treat mild or moderate gastroparesis. 118. The method of one of embodiments 114-117, wherein said human gastroparesis patients are members of a female gastroparesis treatment group, said method further comprising establishing said female gastroparesis treatment group consisting of female human patients only, and excluding all males, prior to administering the amount of metoclopramide or pharmaceutically acceptable salt thereof to said human gastroparesis patients who are members of said female gastroparesis treatment group. 119. The method of one of embodiments 114-118, wherein the metoclopramide is administered at a daily dose of approximately 40 mg to 80 mg of metoclopramide base per day. 120. The method of one of embodiments 118 or 119, wherein the daily dose of metoclopramide is administered as 1 to 8 intranasal aliquots. 121. The method of one of embodiments 118-120, wherein the daily dose of metoclopramide is administered as aliquots of 25 µL to 150 µL. 122. The method of one of embodiments 118-121, wherein the daily dose of metoclopramide is administered as 3-8 intranasal aliquots. 123. The method of one of embodiments 118-121, wherein the daily dose of metoclopramide is administered as 3-8 intranasal aliquots of about 5 mg to 25 mg of metoclopramide base per aliquot. 124. The method of one of embodiments 118-121, wherein the daily dose of metoclopramide is administered as 3-8 intranasal aliquots of about 10 mg of metoclopramide base per aliquot. 125. The method of embodiment 124, wherein each aliquot has a volume of about 50 µL. 126. The method of one of embodiments 118-121, wherein the daily dose of metoclopramide is administered as 4 aliquots of about 14 mg metoclopramide base per aliquot. 127. The method of embodiment 126, wherein each aliquot has a volume of approximately 70 µL. 128. The method of one of embodiments 118-127, wherein the female gastroparesis is female diabetic gastroparesis. 129. The method of one of embodiments 118-128, wherein the method improves quality of life of a subject afflicted with female gastroparesis. 130. The method of one of embodiments 118-129, wherein two or more symptoms of female gastroparesis are treated and said one or more symptoms that are treated are: a. upper abdominal pain associated with female gastroparesis; b. nausea associated with female gastroparesis; c. bloating associated with female gastroparesis; d. satiety associated with female gastroparesis; e. vomiting associated with female gastroparesis; f retching associated with female gastroparesis; g. feeling full (inability to finish a meal) associated with female gastroparesis; h. loss of appetite associated with female gastroparesis; i. stomach fullness associated with female gastroparesis; j. stomach being visibly larger associated with female gastroparesis; and/or k. upper abdominal discomfort associated with female gastroparesis, wherein at least one of said symptoms is upper abdominal pain or nausea. 131. The method of embodiment 130, wherein such administration is oral, buccal, sublingual, intranasal, pulmonary, topical, transdermal, rectal or intravenous. 132. The method of embodiment 130, wherein such administration is intranasal. 133. The method of one of embodiments 130-132, wherein the effective amount of metoclopramide is ineffective to treat male gastroparesis. 134. The method of one of embodiments 130-133, wherein the metoclopramide is administered at a daily dose of approximately 20 mg to 100 mg of metoclopramide base per day. 135. The method of one of embodiments 130-133, wherein the metoclopramide is administered at a daily dose of approximately 40 mg to 80 mg of metoclopramide base per day. 136. The method of one of embodiments 130-134, wherein the daily dose of metoclopramide is administered as 1 to 8 intranasal aliquots. 137. The method of one of embodiments 130-136, wherein the daily dose of metoclopramide is administered as aliquots of 25 µL to 150 µL. 138. The method of one of embodiments 130-137, wherein the daily dose of metoclopramide is administered as 3-8 intranasal aliquots. 139. The method of one of embodiments 130-137, wherein the daily dose of metoclopramide is administered as 3-8 intranasal aliquots of about 5 mg to 25 mg of metoclopramide base per aliquot. 140. The method of one of embodiments 130-137, wherein the daily dose of metoclopramide is administered as 3-8 intranasal aliquots of about 10 mg of metoclopramide base per aliquot. 141. The method of embodiment 140, wherein each aliquot has a volume of about 50 µL. 142. The method of one of embodiments 130-137, wherein the daily dose of metoclopramide is administered as 4 aliquots of about 14 mg metoclopramide base per aliquot. 143. The method of embodiment 142, wherein each aliquot has a volume of approximately 70 µL. 144. The method of one of embodiments 130-143, wherein the female gastroparesis is female diabetic gastroparesis. 145. The method of any one of embodiments 114-144, wherein upper abdominal pain and nausea are treated. 146. A method of treating upper abdominal pain, nausea, or both, in patients having severe gastroparesis in human patients, comprising: a. establishing a group consisting of human patients diagnosed with, or suspected of having, gastroparesis, and excluding human patients diagnosed with, or suspected of having, mild to moderate gastroparesis to form a treatment group consisting of human patients diagnosed with, or suspected of having, severe gastroparesis; b. administering to patients in said treatment group an amount of metoclopramide, or pharmaceutically acceptable salt thereof, effective to treat said moderate to severe gastroparesis; and c. not administering said metoclopramide, or pharmaceutically acceptable salt thereof, to said human patients diagnosed with, or suspected of having, mild gastroparesis. 147. The method of embodiment 146, wherein said metoclopramide, or pharmaceutically acceptable salt thereof, is administered intranasally. 148. The method of embodiment 146 or embodiment 147, wherein said treatment group consisting of human patients diagnosed with, or suspected of having, severe gastroparesis, and excluding human patients diagnosed with, or suspected of having, mild to moderate gastroparesis, excludes all male patients. 149. The method of any one of embodiments 146-148, wherein upper abdominal pain and nausea are treated. 150. A method of increasing the percentage of patients positively responding to metoclopramide administration in a gastroparesis patient population comprising: a. selecting from the total gastroparesis patient population, a treatment group consisting of patients having moderate to severe gastroparesis; and intranasally administering to patients in the treatment group; b. intranasally administering only to patients in the treatment group, a dose of 5 mg to 20 mg of intranasal metoclopramide, or a pharmaceutically acceptable salt thereof, 1 to 4 times per day, for a period of 1 to 12 weeks. 151. The method of embodiment 150, further comprising: administering to patients having gastroparesis, who are not in the treatment group, a standard of care. 152. The method of embodiment 151, wherein the standard of care is selected from the group consisting of oral or intravenous metoclopramide, pro-motility medications, antiemetic medications, pain medications, tricyclic antidepressants, specific meal plans or foods to consume/avoid, controlling glucose levels, correcting thyroid deficiencies, electrical pacing, and surgery. 153. The method of embodiment 150, wherein the dose is 10 mg or 14 mg. 154. The method of embodiment 150, wherein the treatment group consists of female patients having moderate to severe gastroparesis. 155. The method of embodiment 154, wherein the treatment group consists of diabetic female patients having moderate to severe gastroparesis. 156. The method of embodiment 150, wherein the intranasal metoclopramide administration treats one or more symptoms selected from the group consisting of nausea, bloating, early satiety, vomiting, feeling full, loss of appetite, stomach fullness, stomach being visibly larger, and upper abdominal discomfort. 157. A method of treating symptoms associated with gastroparesis, comprising: a. selecting human patients diagnosed with gastroparesis; b. selecting from the human patients diagnosed with gastroparesis a treatment group consisting of moderate to severe gastroparesis; c. intranasally administering only to patients in the treatment group a dose of 5 mg to 20 mg of intranasal metoclopramide, or a pharmaceutically acceptable salt thereof, 1 to 4 times per day, for a period of 1 to 12 weeks; and d. administering to patients diagnosed with gastroparesis, who are not in the treatment group, a standard of care. 158. The method of embodiment 157, wherein the standard of care is selected from the group consisting of oral or intravenous metoclopramide, pro-motility medications, antiemetic medications, pain medications, tricyclic antidepressants, specific meal plans or foods to consume/avoid, controlling glucose levels, correcting thyroid deficiencies, electrical pacing, and surgery. 159. The method of embodiment 158, wherein the dose is 10 mg or 14 mg. 160. The method of embodiment 158, wherein the treatment group consists of female patients having moderate to severe gastroparesis. 161. The method of embodiment 158, wherein the treatment group consists of diabetic female patients having moderate to severe gastroparesis. 162. The method of embodiment 158, wherein the intranasal metoclopramide administration treats one or more symptoms selected from the group consisting of nausea, bloating, early satiety, vomiting, feeling full, loss of appetite, stomach fullness, stomach being visibly larger, and upper abdominal discomfort.

What is claimed is:

1. A method for treating symptoms associated with moderate to severe gastroparesis, the method comprising:
   intranasally administering to a patient having moderate to severe gastroparesis, a dose of 5 mg to 20 mg of intranasal metoclopramide, or a pharmaceutically acceptable salt thereof, 1 to 4 times per day, for a period of 1 to 12 weeks,
   wherein a patient having moderate to severe gastroparesis is defined by the Modified Gastroparesis Cardinal Symptom Index-Daily Diary (mGCSI-DD) or Gastroparesis Symptom Assessment (GSA) as a patient having an mGCSI-DD score of 3 or greater and/or a GSA score of 2.7 or greater.

2. The method of claim 1, wherein the patient is receiving a standard of care for treating gastroparesis and/or has received a standard of care for treating gastroparesis,
   wherein the standard of care for treating gastroparesis is selected from the group consisting of oral or intravenous metoclopramide, pro-motility medications, antiemetic medications, pain medications, tricyclic antidepressants, specific meal plans or foods to consume/avoid, controlling glucose levels, correcting thyroid deficiencies, electrical pacing, and surgery.

3. The method of claim 1, wherein the intranasal metoclopramide administration treats one or more symptoms selected from the group consisting of nausea, bloating, early satiety, vomiting, feeling full, loss of appetite, stomach fullness, stomach being visibly larger, and upper abdominal discomfort.

4. The method of claim 1, wherein the patient has an mGCSI-DD score of approximately 4 or greater.

5. The method of claim 1, wherein the symptoms associated with gastroparesis comprise one or more of:
   (a) upper abdominal pain associated with female gastroparesis;
   (b) nausea associated with female gastroparesis;
   (c) bloating associated with female gastroparesis;
   (d) satiety associated with female gastroparesis;
   (e) vomiting associated with female gastroparesis;
   (f) retching associated with female gastroparesis;
   (g) feeling full associated with female gastroparesis;
   (h) loss of appetite associated with female gastroparesis;
   (i) stomach fullness associated with female gastroparesis;
   (j) stomach being visibly larger associated with female gastroparesis; and/or
   (k) upper abdominal discomfort associated with female gastroparesis.

6. The method of claim 1, wherein severity of the gastroparesis is assessed by the mGCSI-DD and/or by the GSA, and by one or more of questioning the patients regarding symptoms of gastroparesis by a Patient Reported Outcome (PRO) symptom measurement instrument, a gastrointestinal disorders-symptom severity index (PAGI-SYM), octanoic breath test, wireless capsule endoscopy, radioscintigraphy, ultrasonography, x-rays employing a radiopaque marker, a physician reported outcome measurement tool, and/or by physician clinical assessment.

7. The method of claim 6, wherein the radiopaque marker is barium.

8. The method of claim 6, wherein the PRO symptom measurement instrument comprises daily recordation of signs and symptoms.

9. The method of claim 6, wherein the PRO symptom measurement instrument comprises rating all signs and symptoms except vomiting by severity and rating vomiting by frequency rather than severity.

10. The method of claim 1, wherein a daily dose of metoclopramide is about 30 mg/day to about 80 mg/day.

11. The method of claim 10, wherein the patient is administered the dose 1, 2, 3, or 4 times per day.

12. The method of claim 11, wherein the dose has a volume of about 25 µL to 150 µL.

13. The method of claim 12, wherein the dose has a volume of about 70 µl.

14. The method of claim 1, wherein each dose comprises about 10 mg, about 14 mg, or about 15 mg.

15. The method of claim 14, wherein the patient is administered the dose 1, 2, 3, or 4 times per day.

16. The method of claim 15, wherein the dose has a volume of about 25 µL to 150 µL.

17. The method of claim 16, wherein the dose has a volume of about 70 µl.

* * * * *